(12) United States Patent
Kjærulff et al.

(10) Patent No.: US 8,860,938 B2
(45) Date of Patent: Oct. 14, 2014

(54) APPARATUS AND METHODS FOR ANALYSING FLUORESCENT PARTICLES

(75) Inventors: Søren Kjærulff, Hillerod (DK); Mette Elena Skinderso, Virum (DK); Helle Frobøse Sørensen, Copenhagen V (DK); Frans Ejner Ravn, Frederiksberg (DK); Martin Glensbjerg, Bronshoj (DK)

(73) Assignee: ChemoMetec A/S, Allerød (DK)

( * ) Notice: Subject to any disclaimer, the term of this patent is extended or adjusted under 35 U.S.C. 154(b) by 580 days.

(21) Appl. No.: 13/123,560

(22) PCT Filed: Oct. 21, 2009

(86) PCT No.: PCT/DK2009/050278
§ 371 (c)(1),
(2), (4) Date: Nov. 4, 2011

(87) PCT Pub. No.: WO2010/045949
PCT Pub. Date: Apr. 29, 2010

(65) Prior Publication Data
US 2012/0045757 A1    Feb. 23, 2012

(30) Foreign Application Priority Data

Oct. 21, 2008    (DK) .................................. 2008 01464

(51) Int. Cl.
*G01N 1/10* (2006.01)
*G02B 27/09* (2006.01)
*G01N 21/64* (2006.01)

(52) U.S. Cl.
CPC .... *G01N 21/6458* (2013.01); *G01N 2021/6419* (2013.01); *G02B 27/0905* (2013.01); *G02B 27/0961* (2013.01); *G01N 2021/6421* (2013.01); *G01N 2201/0631* (2013.01); *G01N 2021/6478* (2013.01); *G01N 2021/6441* (2013.01)
USPC ......................................................... 356/246

(58) Field of Classification Search
USPC ......................................................... 356/246
See application file for complete search history.

(56) References Cited

U.S. PATENT DOCUMENTS 4,180,060 A    12/1979    Kutter
4,293,892 A    10/1981    Plummer
(Continued)

FOREIGN PATENT DOCUMENTS

EP    1 316 793    6/2003
EP    1 754 997    2/2007
(Continued)

OTHER PUBLICATIONS

Casparri et al., 2006, "Multiparametric cell cycle analysis by automated microscopy", J. Biomol. Screen., 11, pp. 586-598.
(Continued)

*Primary Examiner* — Tarifur Chowdhury
*Assistant Examiner* — Omar Nixon
(74) *Attorney, Agent, or Firm* — Gifford, Krass, Sprinkle, Anderson & Citkowski, P.C.

(57) ABSTRACT

According to an embodiment of the invention, an apparatus to detect fluorescence from a sample is disclosed. The apparatus comprises a sample plane onto which the sample is arranged, an excitation light unit including at least a light source to illuminate the sample, and a detection unit comprising at least a detector having at least 100,000 active detection elements to detect a fluorescence signal from the sample.

28 Claims, 27 Drawing Sheets

(56) References Cited

U.S. PATENT DOCUMENTS

| | | | |
|---|---|---|---|
| 5,867,266 A * | 2/1999 | Craighead | 356/344 |
| 6,403,378 B1 | 6/2002 | Phi-Wilson et al. | |
| 7,068,365 B2 * | 6/2006 | Hansen et al. | 356/246 |
| 2003/0103662 A1 | 6/2003 | Finkbelner | |
| 2005/0237521 A1 | 10/2005 | Hirono | |
| 2006/0256340 A1 | 11/2006 | Hansen et al. | |
| 2008/0193930 A1 | 8/2008 | Ornatsky et al. | |

FOREIGN PATENT DOCUMENTS

| | | |
|---|---|---|
| JP | 2003-337286 | 11/2003 |
| WO | WO 00/28297 | 5/2000 |
| WO | WO 03/021212 | 3/2003 |

OTHER PUBLICATIONS

Cohen, 1997, "Caspases: the executioners of apoptosis", Biochem J, 326, pp. 1-16.

Cossarizza et al., 1993, "New method for the cytofluorimetric analysis of mitochondrial membrane potential using the J-aggregate forming lipophilic cation 5,5',6,6'-tetrachloro-1,1',3,3'-tetraethylbenzimidazolcarbocyanine iodide (JC-1)", Biochem Biophys Res Commun 197 pp. 40-45.

Davies, 1991, "A comparison of fluorochromes for direct viable counts by image analysis", Letters in Applied Microbiology, 13, pp. 58-61.

Galladro-Escarate et al, 2007, "Relationship between DAPI-fluorescence fading and nuclear DNA content: An alternative method to DNA quantification", Biol Res, 40, pp. 29-40.

Gavrieli et al., 1992, "Identification of programmed cell death in situ via specific labeling of nuclear DNA fragmentation", J Cell Biol, 119, 3, pp. 493-504.

Kapuscinski et al., 1982, "Luminescence of the solid complexes of acridine orange with RNA". Cytometry 2, pp. 201-211.

Lassus et al., 2002, "Requirement for caspse-2 in stress-induced apoptosis before mitochondrial permeabilization", Science, 297, pp. 1352-1354.

Liu et al, 2008, "Transient transfection factors for high-level recombinant protein production in suspension cultured mammalian cells", Mol. Biotechnol, 39, pp. 141-153.

McCarthy et al., 1988, "Flow cytometry techniques in radiation biology", Toxicology Letters, 43, pp. 219-233.

Millot et al., 1997, "Characterization of Acidic Vesicles in Multidrug-resistant and Sensitive Cancer Cells by Acridine Orange Staining and Confocal Microspectrofluorometry". The Journal of Histochemistry & Cytochemistry 45(9): pp. 1255-1264.

Moussa et al., 2004, "Evaluation of viability and apaptosis in horse embryos stored under different conditions at 5 degree C", Theriogenology, 61, pp. 921-932.

Nicholson et al., 1995, "Identification and inhibition of the ICE/CED-3 protease necessary for mammalian apoptosis", Nature, 376, pp. 37-43.

Preckel, 2001, "Monitoring transfection efficiency in cells using an on-chip staining protocol", Agilent Technologies, pp. 1-8.

Puchkov, 2006, "The viability assessment of ethanol-producing yest by computer-aided fluorescence microscopy", Microbiology, 75, 2, pp. 154-160.

Reers et al., 1991, "J-aggregate formation of a carbocyanine as a quantitative fluorescent indicator of membrane potential", Biochemistry, 30, pp. 4480-4486.

Renehan et al., 2001, "What is apoptosis, and why is it important?", BMJ, 322, pp. 1536-1538.

Reutelingsperger et al., 2002, "Visualization of cell death in vivo with the annexin A5 imaging protocol", J Immunol Methods, 265, pp. 123-132.

Schilling et al., 1979, "DAPI—a further fluorescence test for diagnosing the viability of early cow and rabbit embryos", Zuchthyg., 14, pp. 170-172.

Seppi, 1991, "Evidence for membrane protein oxidation during in vivo aging of human erythrocytes", Mechanisms of Ageing and Development, Elsevier Sequoia, Lausanne CH, 57, pp. 247-258.

Shapiro et al, 2001, "Violet laser diodes as light sources for cytrometry", Cytometry, 44, pp. 133-136.

Tarnowski et al., 1991, "DAPI as a useful stain for nuclear quantitation". Biotech Histochem, 66, pp. 296-302.

van Engeland et al., 1998, "Annexin V-affinity assay: a review on an apoptosis detection system based on phosphatidylserine exposure", Cytometry, 31, 1, pp. 1-9.

* cited by examiner

A

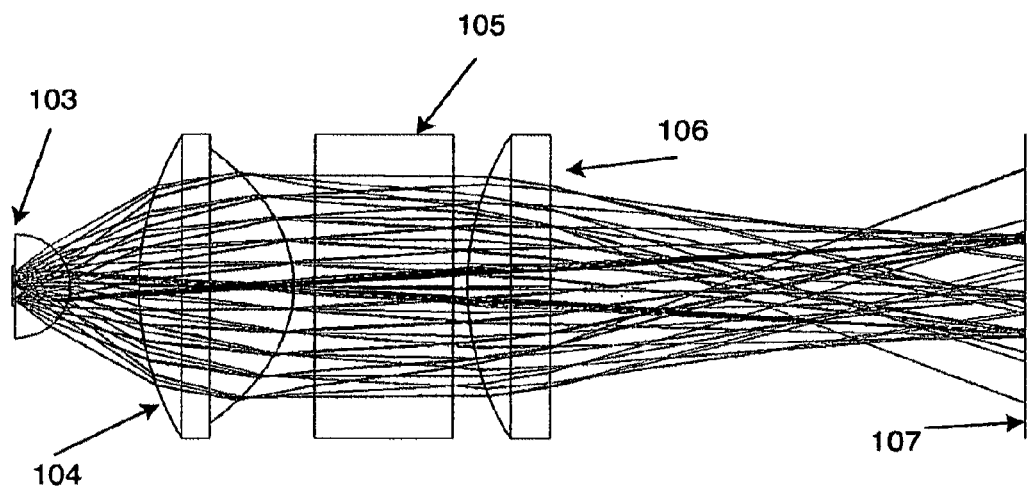
B
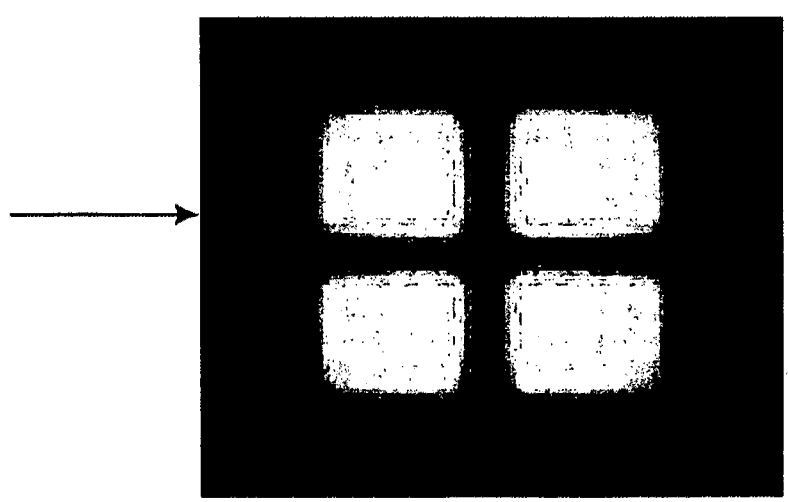
C
Figure 1 (contd.)

401  402  403  404  405  406

A

B

A

B

Jurkat, AO

Jurkat, DAPI

Jurkat, AO (green) and
DAPI (blue)

APPARATUS AND METHODS FOR ANALYSING FLUORESCENT PARTICLES

CROSS-REFERENCE TO RELATED APPLICATIONS

This application is the U.S. National Phase of PCT/DK2009/050278 filed Oct. 21, 2009, which claims priority of Danish Patent Application PA 2008 01464 filed Oct. 21, 2008.

FIELD OF THE INVENTION

The present invention relates to a particle analyzer. More particularly, the invention relates to a method and an apparatus for analysis of particles, such as biological particles.

BACKGROUND OF THE INVENTION

Many modern techniques of biochemistry and biotechnology are based on the analysis of biological particles, e.g. cells. Several parameters concerning the type or species of the particles, as well as the state of the particles, such as viability, are among parameters and properties that are routinely investigated. Further information about intercellular status is also frequently determined. In this field, the method of luminescence detection, e.g. fluorescence detection, has gained a wide application, mainly due to its inherent specificity and sensitivity.

Photoluminescent analysis of material, such as biological material, is based on illuminating a sample with light (excitation) of a given wavelength and collecting light emitted (emission) from the sample, parts or components of the sample, at another substantially different wavelength. The difference in wavelength between excitation and emission (generally called Stoke's shift) is a property of the sample being analysed, more generally a property of the photoluminescent molecules present in the sample. If the Stoke's shift is great enough to allow substantial optical separation of excitation and emission light, it is feasible to use the method of photoluminescence for the analysis of the material.

The photoluminescent emission (e.g. phosphoresce or fluorescence) is typically low in intensity compared to the excitation light, usually by the order of several magnitudes. The fact that emission is detected against "darkness", makes the method well suited, since many of the detectors commercially available show low response to "darkness" while responding considerably well to light, e.g. photons, striking the detector. Nevertheless improved sensitivity, e.g. expressed as increased emission, is typically a favourable property and therefore there exist currently numerous methods for that purpose in the prior art.

Increase in the intensity of excitation light generally increases the amount of emitted light, since the probability of generating emission is proportional with the number of photons interacting with photoluminescent molecules. One often used method for the increase of excitation intensity is the use of laser, which are available in configurations where the amount of emitted light is strong, both since the amount of emitted light, e.g. expressed as energy flux, is considerable, but also since the light from a laser is easily focused onto a small area, thus generating high light density, e.g. expressed as emitted energy per area.

Another method for illumination of photoluminescent material is to use a dispersed light source, such as a lamp or a light emitting diode. The advantage of such light sources is that they emit dispersed light, thus allowing the illumination of a considerably large area. One common drawback to these light sources has typically been the relatively poor degree of homogeneous illumination of the sample material, obtained simultaneously with high degree of efficiency, defined by the fraction of emitted light striking the sample material.

Often preferred equipment for biological analyses is a microscope, typically equipped with two or more objectives for variable magnifications. Further, fluorescence detection requires a wavelength specific excitation and emission filters. The operation of a microscope has to some degree been automated, mainly through the implementation of image analysis. However, even with such automation, the operation of a microscope is primarily a manual task, requiring considerable training of the operator.

Automated flow cytometers are also used for analyzing particles such as cells. Flow cytometer is a synonym for a wide range of equipment characterised by analysing particles under flow conditions, where these conditions usually allow individual particles to be analysed one at a time. Flow cytometer in certain versions make complex analyses of biological particles available, but flow cytometers are difficult to use because the operation usually requires considerable operator skill.

The apparatus and method of the present invention also addresses the areas of cell viability. The determination of cell viability is important for assessing the effects of e.g. drugs, environmental pollutants, temperature, ionic extremes and radiation on cells and tissues. Cell membrane integrity is commonly used as indicator of cell viability. A feature of loss of membrane integrity is the formation of pores that permit the passage of low molecular weight molecules (MW<2000 Daltons) in and out of the cell. The enhanced permeability has been the basis for many cell viability assays. The most common methods used for viability measurements are $^{51}$Cr release, Trypan blue exclusion and the combination of different fluorescent dyes to detect live and dead cells. U.S. Pat. No. 6,403,378 describes a method based on membrane integrity that utilizes two fluorescent dyes, one which labels all dead cells with compromised membranes while the other labels all living cells. To obtain reliable results for different cell populations and densities using a two-dye method it is crucial to carefully control the amount of each dye and the incubation time used to stain the cells. Propidium iodide and ethidium bromide are excluded from the cytosol, and hence the nucleus, of viable cells and are mentioned as the most common fluorescent tracers for staining dead cells. In contrast, acridine orange and Hoechst-33342 are readily taken up by viable cells and are often used as fluorescent probes for staining living cells.

Acridine orange (IUPAC name: N,N,N',N'-tetramethylacridine-3,6-diamine, synonyms: Basic Orange 3RN, Euchrysine, Acridine Orange NO, Rhodulin Orange NO, Waxoline Orange etc.) is a nucleic acid selective fluorescent cationic dye that interacts with DNA and RNA by intercalation or electrostatic attractions. When bound to double stranded DNA and RNA acridine orange has excitation maximum at 502 nm and an emission maximum at 525 nm. When it associates with single stranded nucleic acid, the excitation maximum shifts to 460 nm and the emission maximum shifts to 650 nm. Acridine orange is also known to show alterations of absorbance and fluorescence properties in its different forms. The monomeric dye in solution exhibits a green fluorescence, whereas the stacking of acridine orange in oligomeric structures will have a red emission (Kapuscinski et al., 1982: *Luminescence of the solid complexes of acridine orange with RNA. Cytometry* 2, pp. 201-211). This alteration results from a concentration-dependent increase in resonance energy transfer among individual acridine orange molecules, and increasing concentrations of acridine orange in a solution will induce progressive quenching of the green emmission (Millot et al., 1997: *Characterization of Acidic Vesicles in Multidrug-resistant and Sensitive Cancer Cells by Acridine Orange Staining and Confocal Microspectrofluorometry. The Journal of Histochemistry & Cytochemistry* 45(9): pp. 1255-1264). Acridine orange will also enter acidic compartments such as lysosomes and become protonated and sequestered. In these low pH conditions, the dye will emit red light when exited by blue light. In conclusion, this shows that the fluorescence emission spectrum of acridine orange is affected by many factors, including the gross secondary structure of the polynucleotides, pH and the concentration of acridine orange.

DAPI or 4',6-diamidino-2-phenylindole is another fluorescent dye that has been described as cell permeable and useful for staining of living cells (e.g. Betty I. Tarnowski; Francis G. Spinale; James H. Nicholson. 1991. *Biotechnic and Histochemistry,* 66: 296-302). However, careful studies in our laboratories have revealed that DAPI penetrates cells with a rather slow kinetics. Thus, by controlling the concentration and incubation time DAPI can be used as a probe for staining nonviable cells and can therefore be used to discriminate between live and dead cells. DAPI preferentially binds to double stranded DNA and associates with AT clusters in the minor groove. When bound to double-stranded DNA its absorption maximum is at 358 nm and its emission maximum is at 461 nm. Binding of DAPI to DNA produces a 20-fold fluorescence enhancement. DAPI will also associate to RNA, though in a different binding mode. The emission peak of the DAPI/RNA complex is red-shifted to around 500 nm and the quantum yield is only 20% of that of the DAPI/DNA complex.

The combination of acridine orange and DAPI has not previously suggested been as or demonstrated to be suitable for a simultaneous or two-color fluorescence assay of cell viability.

The apparatus and method of the present invention also addresses the areas of transfection. Transfection, the introduction of foreign nucleic acid (DNA or RNA) into a eukaryotic cell, is a common and important laboratory procedure for studying the gene and protein function in living cells. There are numerous methods available for cell transfection such as formation of complexes of the nucleic acid with either DEAE dextran or calcium phosphate to allow cell uptake by endocytosis, or eletroporation, which employs pulses of voltage to form pores in the plasma membrane through which the nucleic acid can enter. Most transfection procedures, however, involve complexes of nucleic acids and cationic lipids followed by fusion with cells and delivery of DNA/RNA into the cytosol. While rather routine, transfection requires optimization of assay conditions for different cell types. There are a variety of methods for determining transfection efficiency in cell populations. Most of these monitor the expression of a fluorescent, luminescent or colorimetric reporter gene. The reporter gene can be present on the same vector as the gene of interest or on a separate vector. Convenient reporter genes for measuring transfection efficiency is autofluorescent proteins, e.g. green fluorescent protein (GFP) isolated from the jelly fish *Aequorea victoria* and red fluorescent protein (RFP) developed from the marine anemone *Discosoma striata*, both of which enable assays on living cells and requires no substrate for generation of fluorescence. When excited by blue light, GFP emits green light, whereas RFP emits orange/red light when excited with green light. Moreover, the combination of GFP with appropriate dyes allows multiplex analysis to estimate e.g. viability, cytotoxicity and apoptosis.

Another approach for monitoring transfection efficiency employs fluorescently labeled nucleic acids as reporter, e.g. Cy5-labeled siRNA to optimize RNAi silencing experiments.

In one method of analysis, the GFP transfected cells are incubated with DACM and propidium iodide (PI). DACM reacts with thiols, the level of which is low in dying/dead cells, to produce a blue fluorescent product in living cells. In contrast, PI only penetrates cells with damaged membranes and, thus, only labels DNA of dead cells. Cells labeled with DACM are detected by UV/violet excitation and measuring blue light, whereas PI labeled cells are detected by green light excitation and measuring the emitted red light. Cells expressing GFP (transfected cells) are monitored by blue light excitation and measuring green light. Information about transfection efficiency and e.g. viability can be extracted from the data.

In another method of analysis, the RFP transfected cells are incubated with DACM and acrdine homodimer. Acridine homodimer only penetrates cells with damaged membranes and, thus, only labels dead cells. Living cells labeled with DACM are detected by UV/violet excitation and measuring blue light, whereas dead cells labeled with acridine homodimer are detected by blue light excitation and measuring the emitted green light. Cells expressing RFP (transfected cells) are monitored by green light excitation and measuring red light. Information about transfection efficiency and e.g. viability can be obtained from the data.

In a third method of analysis, cells transfected with siRNA, labeled with a green fluorophore, e.g. FITC, are incubated with DACM and PI. Living cells labeled with DACM are detected by UV/violet excitation and measuring blue light, whereas dead cells labeled with PI are detected by green light excitation and measuring the emitted red light. Cells harboring siRNA (transfected cells) are monitored by blue light excitation and measuring green light. Information about transfection efficiency and e.g. viability can be pulled out from the data.

The combination of a thiol-reacting reagent and a cell impermeable DNA stain in a cell population transfected with nucleic acid has not previously been suggested or demonstrated to be suitable for a simultaneous assay of transfection efficiency, cell viability and cytotoxicity.

The apparatus and method of the invention also addresses the area of cell cycle. The cell cycle represents the most fundamental and important process in eucaryotic cells. An ordered set of events, culminating in cell growth and division into two daughter cells, the cell cycle is tightly regulated by defined temporal and spatial expression, localization and destruction of several cell cycle regulators. Cyclins and cyclin-dependent kinases (CDK) are major control switches for the cell cycle, causing the cell to move from $G_1$ to S or $G_2$ to M phases. In a given population, cells will be distributed among three major phases of cell cycle: $G_1/G_0$ phase (one set of paired chromosomes per cell), S phase (DNA synthesis with variable amount of DNA), and G/M phase (two sets of paired 2 chromosomes per cell, prior to cell division).

The most common approach to determine the cell cycle stage is based on measurement of cellular DNA content. DNA content can be determined using fluorescent, DNA-selective stains that exhibit emission signals proportional to DNA mass. Cellular fluorescence is measured by flow, image or laser scanning cytometry. This analysis is typically performed on permeabilized or fixed cells using a cell-impermeant nucleic acid stain, but is also possible using live cells and a cell-permeant nucleic acid stain.

Because cell cycle dysregulation is such a common occurrence in neoplasia, the opportunity to discover new targets for anticancer agents and improved therapeutics has been the focus of intense interest. The cell cycle assay has applicability to a variety of areas of life science research and drug development, including cancer biology, apoptosis analysis, drug screening and measuring health status of cell cultures, e.g. in bioreactors.

DAPI is a competent dye for measurement of the cell cycle stage. However, excitation of DAPI requires a UV light source and standard flow cytometers usually come without a UV light source hampering the use of DAPI.

The apparatus and method of the invention also addresses the area of cell death. Cell death may occur by two distinct mechanisms, necrosis or apoptosis. Necrosis occurs when cells are exposed to harsh physical or chemical stress (e.g., hypothermia, hypoxia) while apoptosis is a tightly controlled biochemical process by which cells are eliminated and where the cell is an active participant in its own termination ("cellular suicide"). Apoptosis is one of the main types of programmed cell death which occur in multicellular organisms and is characterized by a series of events that lead to a variety of morphological changes, including blebbing, nuclear fragmentation, chromatin condensation, cell shrinkage, loss of membrane asymmetry and translocation of the membrane phospholipid phosphatidylserine (PS) from the inner to the outer leaflet of the plasma membrane.

Apoptosis is both a very complex and very important process and dysregulations in the apoptosis machinery may lead to very severe diseases. A growing body of evidence suggests that resistance to apoptosis is a feature of most, if not all types of cancer. Moreover, defects in apoptosis signaling contribute to drug resistance of tumor cells. In the other hand may hyperactivity of the apoptotic processes also cause diseases such as neurodegenerative diseases as seen in Parkinson's or Alzheimer's Diseases, where apoptosis is thought to account for much of the cell death and the progressive loss of neurons.

As apoptosis play a very important role in a wide array of biological processes, including embryogenesis, ageing, and many diseases, this type of programmed cell death is the subject for many studies, and tools for easy detection and investigation of apoptosis are desirable.

SUMMARY OF THE INVENTION

One embodiment of the present invention relates to an apparatus to detect fluorescence from a sample, said apparatus comprising a sample plane onto which the sample is arranged, an excitation light unit including at least a light source to illuminate the sample, and a detection unit comprising at least a detector having at least 100,000 active detection elements to detect a fluorescence signal from the sample.

Another embodiment of the invention relates to an apparatus to illuminate a sample, said apparatus comprising a sample plane having an illumination region onto which the sample is arranged; an excitation unit having a light source to generate an excitation light; and an optical system comprising a lens unit, having a micro lens array where the micro lens array comprises a plurality of lenses arranged in a two dimension arrangement, to receive the excitation light and generate an illumination light that is directed towards the illumination region; wherein, the lens unit produces a homogeneous illumination light to be projected on the illumination region of the sample plane with a high illumination efficiency.

In one embodiment of the invention, a method for illuminating a sample is explained. The method comprises of arranging a sample on a sample plane having an illumination region of at least 0.5 mm$^2$; generating an excitation light using an excitation unit having a light source; and generating an illumination light, directed towards the illumination region, using a lens unit that comprises of a micro lens array having a plurality of lenses arranged in a two dimension arrangement; wherein, the lens unit produces a homogeneous illumination light to be projected on the illumination region of the sample plane with a high illumination efficiency.

In another embodiment of the present invention, a method for detecting fluorescence from a sample is described. The method comprises of arranging a sample on a sample plane, illuminating the sample with an excitation light using an excitation light unit having at least a light source, and detecting a fluorescence signal from the sample using a detection unit comprising at least a detector having at least 100,000 active detection elements.

BRIEF DESCRIPTION OF THE DRAWINGS

The embodiments of the invention, together with its advantages, may be best understood from the following detailed description taken in conjunction with the accompanying figures in which.

DETAILED DESCRIPTION OF THE INVENTION

Figure 1:
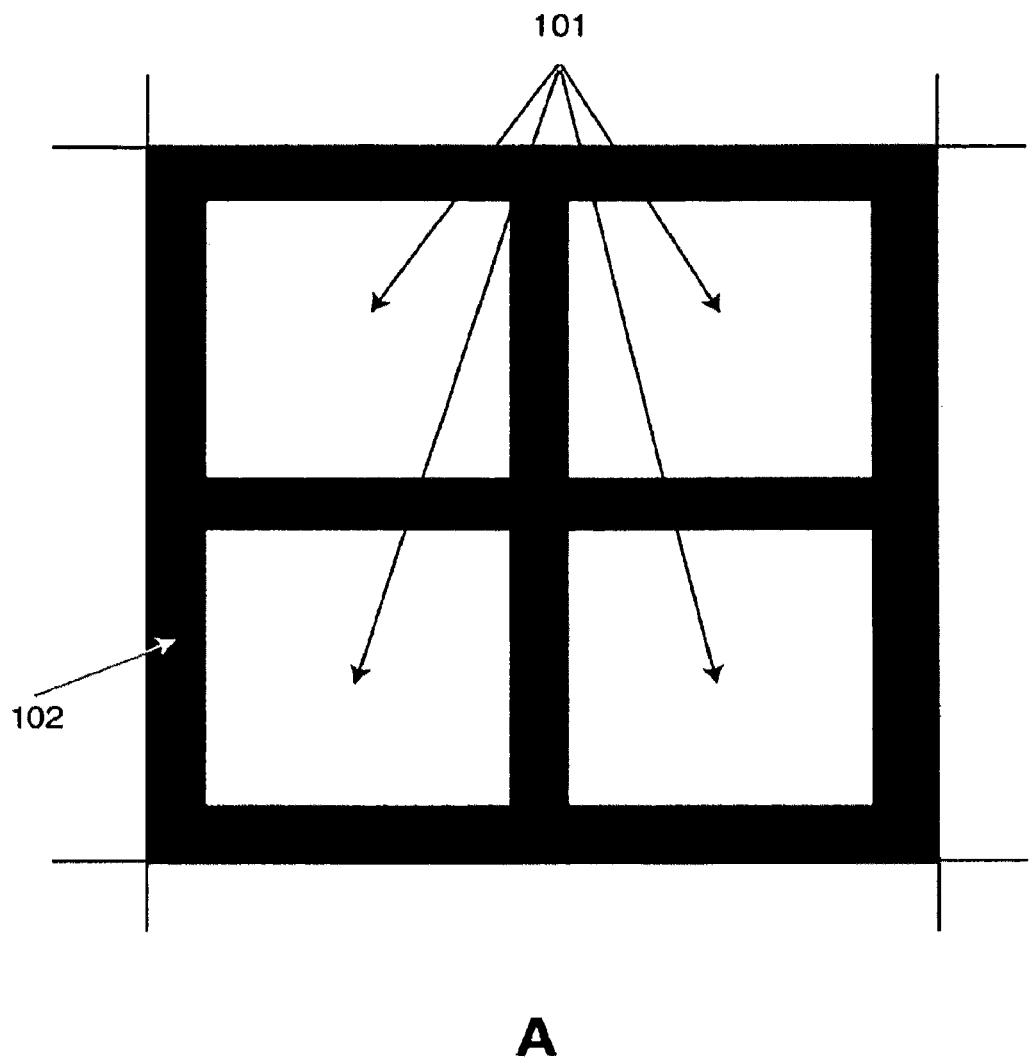
FIG. 1 illustrates a light source for the illumination of a sample and a prior art apparatus system for focusing the illumination light onto sample material.

The object and advantages of the present invention will become apparent to those skilled in the art upon reference to the detailed description taken in conjunction with the provided figures.

According to an embodiment of the invention, the apparatus to analyse a sample comprises of a sample plane onto which the sample is arranged, an excitation light unit including at least a light source to illuminate the sample, and a detection unit comprising at least a detector having at least 100,000 active detection elements to detect a fluorescence signal from the sample.

The sample to be analyzed is a solid, or substantially solid, or liquid sample. The sample contains a particle, which is selected from an animal cell, such as a mammalian, insect and fish cell, from a fungi cell, such as a yeast cell and from a bacterium.

In an embodiment of the invention, the particle itself or material contained on or within the particle is photoluminescent active, generating the fluorescence signal when the sample is illuminated with the excitation light. In another embodiment of the invention, the particle is labelled with a photoluminescent active material, preferably a fluorescent material.

The sample or a part of sample is illuminated with the excitation light from a light source, which emits light usually in a substantially narrow wavelength band. In a preferred embodiment, the light source includes a light emitting diodes and/or laser diodes for the illumination of the sample. The light source may also be selected from a solid state light source and a thermal light source. One highly preferred property of the solid state light sources is its considerable illumination efficiency, particularly when illumination in a defined light band is employed. This is typical in fluorescence analysis, where illumination of 90% or more of the light is preferably emitted in a waveband of less than 50 nm, such as 40 nm or less, more preferably in waveband of 20 nm of less such as 10 nm or less, or even 5 nm or less. In particular, laser or laser diodes wavebands of less than 5 nm are preferred, such as waveband of 2 nm or lesser, preferably a waveband of 1 nm or lesser is preferred. Other highly preferred property of solid state light source is its long operation time, e.g. effective operative life time. For example, operation time of light emitting diodes and diode lasers is longer than 2,000 hours, such as 4,000 hours or more, preferably 8,000 hours or more.

The light source is selected from a dispersive light source, an emitting diode, a laser diode, a laser, a thermal light source, and a solid state light source. Further, in yet another embodiment of the invention, the excitation unit includes a plurality of light sources comprising such as at least two different light sources, such as four different light sources, such as at least six different light sources, such as at least eight different light sources, such as at least 10 different light sources, emitting light of different wavelengths.

In one embodiment of the invention, the sample or a part of the sample being analysed is illuminated in a manner, such that the variation of illumination intensity is lesser than a predetermined value but at the same time, and the efficiency of illumination, defined as the fraction of emitted light from the light source illuminating a sample or sample portion being analysed, is higher than a predetermined value.

According to an embodiment of the invention, the sample is illuminated using a lens unit, having a micro lens array where the micro lens array comprises a plurality of lenses arranged in a two dimension arrangement, to receive the excitation light and generate an illumination light that is directed towards an illumination region of the sample plane. The lens unit produces a homogeneous illumination light to be projected on the illumination region of the sample plane with high illumination efficiency.

In an embodiment of the invention, the excitation light focused onto the micro lens array has a divergence angle of 0.1 mrad or less, preferably 0.05 mrad or less, more preferably 0.02 mrad or less. Each of the lenses in the plurality of lenses of the micro lens array produces an image similar in dimensions to the region of the sample being analysed, preferably where the image produced is substantially rectangular. The plurality of lenses of the micro lens array comprises of at least 4 lenses, preferably more than 4 lenses, more preferably more than 50 lenses elements, and even more preferably more than 100 lenses. These lenses are semi-spherical lenses arranged in an array, preferably where two said arrays are arranged in a series, thus forming an array of lenses. The dimension of the lens is in the range from 0.5 to 3 mm, preferably in the range from 1 to 2 mm. The size of the micro lens array is less than 20 mm, the size being the diameter of the lens array in the direction perpendicular to an excitation-sample axis.

In another embodiment of the invention, the lens unit comprises of a first micro lens array in opposite orientation with a second micro lens array. The selection of the first micro lens array and the second micro lens array is based on enhancing illumination efficiency and/or reducing illumination variation and/or integrating an optical feature of a separate optical element into the optical effect of the lens array. The micro lens array is housed in a casing comprising means for arranging and fixing the micro lens array. This casing is usually made of cast polymer. The pattern of the lenses is preferably similar to the shape of beam of the excitation light.

In an embodiment of the invention, the illumination region is at least 2 times larger than the size of emittance area of the light source. The illumination region under investigation is only exposed to the illumination light, thereby avoiding fading of the fluorescence signal. The sample not under investigation is substantially not exposed to illumination, preferably where the illumination results in alteration in chemical and/or physical property of the sample, such as fading of fluorescent signal.

The structure of the light source, with respect to the light emitting part of the light source is of essential importance, in order to obtain illumination with high efficiency and low variation for the illumination of photoluminescence sample material.

Therefore, several highly preferred embodiments of the present invention use "Power LED" light sources with homogeneous emittance element, as available in several commercially available semiconductor light sources (e.g. LZ1-00G105 from LedEgin, XLamp 7090 LEDs from Cree, Luxeon K2 from Lumiled, NS6B083T from Nichia or the Golden Dragon (LD W51 M) from Osram). In general, several preferred embodiments of the present invention include a light selected from a dispersive light source, an emitting diode, a laser diode and a laser, preferably where the emittance element of substantial physical size, such as for instance greater than 0.5 $mm^2$, or even greater than 1.0 $mm^2$.

It is found, that when using light sources where the light emitting elements have distinct structures, such as lamp or a light emitting diode (i.e. LED), or in general light sources, which form an image or structure when focused, that it is possible to illuminate considerably large sample material, while maintaining both highly homogeneous illumination and good efficiency of emitted light. The homogenous illumination is defined by variation in illumination energy across the sample material. The illumination efficiency is defined by the ratio of illumination light to emitted light. The present invention offers substantial improvement of several applications of photoluminecence, such as fluorescent microscopy. By generating strong homogeneous illumination of the sample material it is possible to perform high quality photoluminecence analysis in a faster and simple manner, thus allowing the use of more simple and robust instrumental design.

A dispersive light source, such as LED, emits light in virtually all directions. In order to use such a light source in an application such as fluorescence microscope, it is therefore necessary to focus the light onto the sample material. Such focusing produces an image of the light source, which may be of dimensions comparable to the field of view of the microscope. On the other hand, the intensity of emitted light in the field of view is an image of the light source, and therefore even though it is possible to illuminate the sample material with good efficiency the intensity of the illumination varies considerably from one part of the sample material to another.

An often preferred embodiment of the present invention uses a number of lenses to focus light from a dispersive light source. It is often preferred that such lenses is a number of substantial identical lenses, preferably lenses arranged in a lens array, such as micro lens arrays. Several preferred embodiments of the present invention use two substantially identical micro lens arrays, arranged in a pair with opposite orientation, while other equally preferred embodiments use a single element, comprising micro lens arrays on two opposite surfaces. In an embodiment using a single element of micro lens arrays, the single element is preferably produced by a moulding method, by moulding a substantially optically transparent material, such as glass or polymer.

A preferred property of light transmitted through a micro lens array, is high degree of parallel light, and therefore several preferred embodiments of the present invention include one or more lens element, such as the micro lens array, which increases the degree of parallelism of the light leaving the light source and entering the micro lens array.

In several preferred embodiments of the present invention, using micro lens array elements, the micro lens arrays on both sides is substantially identical in form, and preferably also in position, while in other equally preferred embodiments the form and/or position of the elements of the micro lens arrays are substantially different, preferable where such difference enhances illumination efficiency and/or reduces illumination variation and/or integrates an optical feature of a separate optical element, such as a lens, into the optical effect of the micro lens array element.

In several preferred embodiments the image of the light source produced by a lens substantially resembles the region of the sample material which is under investigation, preferably by closely resembling the height/with ratio of the detected photoluminescent region or image.

When using a number of identical lenses, it is often preferred that such lenses are arranged in a single element, e.g. a micro lens array. In addition to using a micro lens array several preferred embodiments of the present invention further include one or more lenses, preferably where the purpose of such one or more lens is to collimate light from the light source and/or to increase the spatial angle through which light from the light source is collected. In other embodiment of the invention, a collimating unit to receive the excitation light and generate a collimated excitation light is provided. The collimating unit includes a lens or an array of lenses. The collimating unit increases spatial angle through which the excitation light from the excitation unit is collected.

One often preferred property of using a number of identical lenses or lens elements, such as micro lens array, is that it is possible to eliminate the imaging of any structure in the light source, such as a filament of a lamp. If such structure is imaged on the sample material the intensity of illuminated light varies in accordance with the imaged structure of the light source. Such structure can not be eliminated by conventional imaging optics and typically would require methods such as defocusing or diffusing of light, where the result of such methods would generally result in reduction of illumination efficiency. Several preferred embodiments of the present invention include micro lens arrays which are comprised in a single element, preferably an element produced by casting optically transparent material, preferably a polymer material in a mould.

When producing a micro lens array element by casting polymer material, it is often preferred to use considerably small thickness. Such small thickness is typically obtained by using small lens elements, such as lens elements of 3 mm or less in diameter, such as 2 mm or less in diameter, even 1 mm or less, such as 0.5 mm or less. Typically such micro lens array element are less than 10 mm in thickness, such as 8 mm or less, such as 5 mm or less, even 3 mm or less. Depending on the method used to produce the mould used for casting, it is often of interest to use lenses of certain diameter, such as lenses of 0.5 mm diameter or more, such as 1 mm or more, such as 2 mm or more, such as 3 mm or more. Thus it is often preferred that the diameter of the lenses is in the range from 0.5 to 3 mm, preferably in the range 1 to 2 mm.

In several preferred embodiments of the present invention, the size of the micro lens array is less than 20 mm, such as 15 mm or less, such as 10 mm, in certain embodiments even smaller, such as 8 mm or less, such as 5 mm or less, the size being the diameter of the lens array in the direction perpendicular to the major axis of illumination.

Several preferred embodiments of the present invention use a single light source, e.g. emitting diode, laser diode or laser as a light source, while other equally preferred embodiments use two or more light sources, preferably is a single assembly. In many of these embodiments it is preferred that the two or more light sources are identical, with respect to optical property, while in other equally preferred embodiments at least two light sources are different, with respect to optical property. Generally two or more identical light sources are able to generate a greater flux of light, while two or more different light sources add flexibility with respect to properties such as wavelength of emitted light.

In other embodiments of the invention, the two or more light sources are arranged relative to at least one other unit of the apparatus and/or to the sample plane. Such arrangement comprises of relative movement of the light source to at least one other unit and/or the sample plane by 1 mm or less. The arrangement arrangement affects homogeneity of the illumination light over the illumination region, preferably where an ideal arrangement results in the minimum illumination variation.

Several preferred embodiments of the present invention include methods for production, which may place the light source relative to at least one of the optical component, in such a manner that satisfactory illumination efficiency and/or variation in illumination intensity is obtained.

This is preferably obtained by including means which allow the light source to be placed in a plane (light source plane) parallel to the illumination region plane, with accuracy in position of better than 1 mm, such as better than 0.5 mm, or even better than 0.2 mm, such as with accuracy variation of 0.1 mm or lower. Also several embodiments include methods for production, which can place the light source and at least one optical element in position relative to each other, in a direction parallel to the main direction of illuminated light. This is preferably obtained by including means with allow the light source and/or at least one optical element to be placed relative to each other, with accuracy in position of better than 0.1 mm, such as better than 0.5 mm, or even better than 0.2 mm, such as with accuracy of 0.1 mm or better.

Often, it is preferred to include a wavelength separating unit, e.g. an optical filter, in illumination means, preferably where the purpose is to define a wavelength region or polarity of illumination light. The wavelength separation unit is a spectral filter means selected from an interference filter, absorbing filter, and excitation filter.

One preferred embodiment of the present invention allows the light source to be placed close to the sample material being analysed. This allows the construction of compact optical system, since the illumination means, including light source and optical components can be shorter than 100 mm in length along the optical axis of the system, preferably shorter than 60 mm, more preferably shorter than 40 mm, preferably even shorter than 20 mm, such as shorter than 15 mm.

Several preferred embodiments of the present invention have the illumination means arranged on, or substantially on the optical axis of a photoluminescent imaging system, preferably in arrangement where the flux of illumination light has a general direction toward the detector system of the imaging system. Other equally preferred embodiments of the present invention have the illumination means arranged substantially off the optical axis of an imaging system, preferably in arrangement including dichroic mirror reflecting the illumination light onto the sample along the axis of the imaging system.

One often preferred property of embodiments of the present invention is that it is possible to illuminate sample material with homogeneous light with high efficiency without the use of diffuser or defocusing element/arrangement. In another embodiment of the invention, the illumination efficiency and illumination variation is obtained without substantial defocusing of the units of the illumination means.

One often preferred property of embodiments of the present invention is that regions of the sample material, not under investigation, are substantially not exposed to illumination. This is often a desirable property, preferably where the result of illumination is alteration in chemical and/or physical property of the sample mater, such as fading of fluorescent signal.

The detection unit, comprising at least a first detector, collects the fluorescence signal, representing an image, from the sample. The first detector detects signals from the sample, thereby acquiring an image of the sample. The detector is an image sensing device, such as a Charge Coupled Device (CCD) or a Complementary Metal Oxide Semiconductor (CMOS) device. The detector is preferably characterised by a preferred dimension of active area, preferred number of active detection elements, e.g. pixels, and preferred responsiveness, e.g. sensitivity to detected light. The apparatus preferably uses one or more lens for the generation of an image of the sample, where the arrangement of such lenses determines the focusing and optical magnification of the system.

In yet another embodiment of the invention, the detector includes an array of active detection elements. These active detection elements are preferably arranged in a two-dimensional arrangement allowing the simultaneous acquisition of spatial information from the sample being analysed. The detector preferably comprises an array of detection elements such as at least 100,000 active detection elements, such as 400,000 active detection elements or more, such as 1,000,000 active detection elements or more, preferably 2,000,000 active detection elements or more. Such high number of the active detection elements is usually preferred when the analyses of the sample includes the determination of spatial information of biological particles in the sample. When the analysis of the sample includes the determination of spatial information of biological particles in the sample, several preferred embodiments of the present sample include active detection elements, which are less than 10 μm in size, the size being the longer of the width or the height of the detection elements, preferably where the size of the active detection elements is 5 μm or less, preferably 3 μm or less.

In another embodiment of the invention, the apparatus includes a first focussing unit/means to focus the excitation light onto the sample. In yet another embodiment of the invention, the apparatus includes a second focusing unit/means to focus the fluorescence signal onto the detection unit. The first focussing unit and second focussing unit is typically a lens or an array of lenses. In many preferred embodiments of the present invention, focusing is performed by moving one or more lenses of the first focussing unit and/or the second focussing unit. The focussing also maintains a substantially fixed length of the apparatus, that is, the distance from a focal plan, where the sample is located, to an image plan, where the detection unit is located. Preferably, the focusing is performed by recording a series of images of a predetermined structure, where the point of focusing is determined by one or more properties of such predetermined structure, such as dimension or intensity. Preferably, the apparatus is characterised in a manner, such that the area of the field of view may be determined or estimated after taking into account the changes in the focusing. In various embodiments of the invention, the first focussing unit and the second focussing unit provide a fixed optical magnification of 40× or less, preferably 20× or less, more preferably 10× or less.

In another embodiment of the invention, it is preferred that the physical length of the apparatus is substantially same even under conditions that allow performance of different optical analysis, such as variable wavelength in transmission or scatter microscopy, variable excitation/emission wavelengths in fluorescence microscopy, magnification or focusing. An apparatus constructed in this manner offers considerable mechanical advantages, such as simpler production and improved mechanical robustness. This is achieved by using one or more of preferred design methods, such as selection of optical components, e.g. with respect to thickness and/or curvature. When producing the apparatus with a fixed physical length, it is typically preferred to allow for adjustment of focusing by moving of one optical component, such as a lens, along the direction of optical path. The degree of focusing is preferably determined by determining imaging property of one or more objects visible in the system, such as determining a size of an image of one or more objects.

Preferred embodiment of the present invention, include apparatus with a fixed optical magnification, preferably where the optical magnification low, such as where it is less than 10 fold, such as 6 fold or less, such as 4 fold or less, such as 2 fold or lesser. Several preferred embodiments of the present invention include apparatus, which produce image at substantially no magnification, that is. one-to-one imaging. Typically low optical magnification is preferred when the particles being analysed are approximately 20 μm or less in size.

In other equally preferred embodiments the optical magnification is 10 fold or greater, such as 15 fold or greater, such as 20 fold or greater. Such optical magnification is typically preferred when analysing small particles, and/or when the signal detected from a particle is low, such as when the number of detectable sites on a particle is considerably low. Typically preferred optical magnification in such analysis is in the range between 10 and 40 fold, such as between 15 and 30 fold.

In another embodiment of the invention, optical magnification of the apparatus, defined by the dimensions of motive and the image of the motive on the detector is of a predetermined magnitude. The magnification may be altered by changing position of one or more units of the apparatus. Preferably, the magnification is changed by moving one or more lens(es). Preferably, the magnification is changed without substantially changing the length of the apparatus, that is, the distance from the focal plan, where the sample is located, to the image plan, where the detection unit is located. The apparatus typically provides a magnification of 40× or less, preferably 20× or less, more preferably 10× or lesser.

In another embodiment of the invention, an excitation light filter is inserted in an excitation light path directed from at least one of the light sources, to separate the excitation light into a plurality of excitation wavelength bands prior to illumination of the sample. The excitation light path is the path from the centre of excitation light beam to the sample plane Similarly, in another embodiment of the invention, an emission light filter may be inserted in an emission light path directed to at least one of the detectors, to separate the fluorescence signal into a plurality of emission wavelength bands prior to the detection of the fluorescence signal at the detection unit. The emission light path is the path from the sample plane to the detection unit.

The excitation light filter and the emission light filter for separation of the excitation light and the fluorescence signal is selected from an interference filter, absorption filter, low pass filter, high pass filter, and band pass filters. In several preferred embodiments, the filters may be high-pass filters, that is, filter substantially transmitting light at high wavelength, while blocking light at low wavelength, typically preferred as emission filters in fluorescence microscopy, low-pass filters, that is, substantially transmitting light at low wavelength while blocking light at high wavelength, typically preferred as excitation filters in fluorescence microscopy. Several preferred embodiments include band-pass filters, e.g. substantially transmission in a wavelength band, while higher and lower wavelengths are blocked, typically such filters are preferred in fluorescence microscopy, where the system under investigation includes multiple excitation and/or emission possibilities.

In several highly preferred embodiments of the present systems, wavelength separation means, facilitate the investigation of two or more properties of a particle, such as identification of a particle or separation of two or more groups of particles. Preferably such identification or separation by wavelength properties is performed by recording two or more images of the same sample, while the sample and the particle of the sample is/are substantially in same geometrical configuration in said two or more images, where said two or more images reflect different or substantially different wavelength properties.

In another embodiment of the invention, wavelength separation means such as filters, facilitate investigation of two or more properties of a particle, such as identification of a particle or separation of two or more groups of particles. Preferably, such identification or separation by wavelength properties is performed by recording two or more images of the same sample, while the sample and the particle of the sample is/are substantially in same geometrical configuration in said two or more images, where said two or more images reflect different or substantially different wavelength properties.

The sample is analyzed at two or more combination of excitation and emission wavebands by selecting a combination of emission light filters and excitation light filters. These combinations allow use of at least one excitation or emission light filters in two or more combinations respectively.

In one preferred embodiment of the present invention, preferably when recording fluorescent information, the emission light filter is arranged on opposite side of the sample being analysed, from the excitation source.

Several embodiments of the present invention include an optical system for fluorescence analysis, where the excitation unit and the detection unit are placed on either side of the sample plane, e.g. transmission fluorescence, as opposed to an arrangement where the excitation unit and the detection unit are on the same side of the sample plane and the excitation light and the emission light are transmitted onto the sample through the use of mirrors and/or lenses, e.g. epifluorescence system. Such transmission fluorescence systems are preferred in several embodiments, typically where they offer simpler mechanical and/or optical arrangement. Although direct alignment of excitation source and detector is often preferred, other embodiments, including substantial alignment, e.g. where divergence from line of parallel arrangement is generally less than 10 degrees, is also implemented.

In another embodiment of the invention, a sample that gives rise to a plurality of spectral information, such as the emittance of fluorescent light at several wavelengths, is analyzed by recording two or more images under conditions where each recorded image substantially contains all wavelengths under consideration, but preferably in different intensities. One preferred way of obtaining this to employ a spectral modulation means in the optical path, preferably by using an interferometer, such as a Michelson interferometer.

Several preferred embodiments of the present invention include means to separate light into two or more wavelength components, where such means include means which modulate light, such as a Michelson and/or Fabry-Perrot interferometer. Several preferred embodiments also include modulation means, such as interferometers, where modulation is generated by changing optical path differences. It is preferred that such path difference is small, such as less than 800 µm, such as 400 µm or less, preferably 200 µm or less, more preferably 100 µm or lesser.

In other embodiments of the present invention, based on limited wavelength resolution, the optical path difference of the modulation means is less than 100 µm, such as 80 µm or less, preferably 40 µm or lesser. In other embodiments of the present invention, based on moderate wavelength resolution, the optical path difference is in the range from 20 µm to 200 µm, preferably in the range 40 µm to 100 µm. In several preferred embodiments, the wavelength resolution obtainable using modulation means is no more than 10 nm, such as 20 nm or smaller, such as 40 nm, or even as small as 80 nm, the resolution being defined as the smallest wavelength difference which can be adequately separated.

Preferred modulation means to separate light allows acquisition of images of modulated light at virtually any optical path difference, preferably with accuracy and resolution in position better than 1 µm, when expressed as optical path difference of the modulation means, such as 0.5 µm or better, preferably 0.1 µm or better, more preferably 0.02 µm or better. At any given optical path difference, the modulation means can substantially maintain optical path difference for a considerable time, preferably for a time which is comparable to exposure time of the detector, such as substantially maintaining optical path difference for 1 ms or more, such as for 10 ms or more, preferably 50 ms or more, more preferably 100 ms or more.

In embodiments where intensity of detected light is low, it is preferred that modulation mean may substantially maintain optical path difference of 200 ms or more, such as 400 ms or more, preferably 600 ms or more, more preferably 800 ms or more. When modulation means include means for the movement of one or more optical component(s), such as a mirror or a beamsplitter, the movement is preferably brought about by one or more piezoelectric actuator(s).

When determining wavelength properties of light using the modulation means, the number of images recorded at different modulation is equal to the number of different wavelength bands of interest, preferably the number of images is greater than the number of different wavebands, such as 2 times the number of wavebands, preferably 3 or 4 times the number of wavebands. In other embodiments of the invention, the number of images recorded at different modulation is more than 4 times the number of wavebands of interest, such as 8 times or more, preferably 10 times or more.

In yet another embodiment of the invention, an actuator to move the sample plane and/or at least one of the units to modulate the light emitted from the sample is used.

In another embodiment of the invention, two or more images of the same sample are recorded, showing different spectral properties, such as emission of fluorescence, where the position of the objects on the recorded image is substantially equal in at least two of the images. When recording images at different spectral wavelengths, such as when recording fluorescent intensities, this makes it possible to relate different spectral information to a specific object or a particle, by combining information from two or more images, representing different, or substantially different spectral wavelengths. When using optical filters to separate spectral wavelengths this feature is difficult to obtain, unless great care is given to the position and alignment of such optical filters, since difference in refractive index usually causes aberration and preferred embodiments of the present invention use optical filter selection means which operate with high accuracy, preferably obtained by the use of mechanical means with small tolerances. A preferred method of compensating for spectral aberration is to change the position of one or more optical components, such as a lens or the detectors, or the sample, in a predetermined manner, thus reducing or compensating for changes in position when recoding images representing two or more spectral properties.

In another embodiment of the invention, an image alignment unit is used. The image alignment unit generates an aligned image from a plurality of images, showing different spectral information, acquired from a plurality of fluorescence signals of the sample obtained under different or substantially different emission conditions. In another embodiment, the apparatus further comprises at least two different emission filters capable of filtering signals emitted from the particles toward the detector. In various embodiments of the invention, the apparatus includes at least 4 different emission filters, such as at least 6 different emission filters, such as at least 10 different emission filters, such as at least 15 different emission filters, such as at least 20 different emission filters.

Where two or more emission or transmission wavebands are used for the analysis of the same sample or sample material, it is preferred to include a method of image alignment. The image alignment generates aligned images of the same sample or sample material acquired under two different or substantially different emission conditions, where difference in the position of an object in the aligned images is less than 10 pixels, such as 8 pixels or less, such as 4 pixels or less, preferably even 2 pixels or less, determined as average difference in position objects. The image alignment may be achieved by applying a predetermined transformation to a collected image, transforming collected image to aligned image. Preferably, said predetermined transformation is derived from the measurement of an image comprising objects, which produce identifiable structure in the collected image, where said objects are visible in images collected under said different emission conditions and maintain their position or relative position during the acquisition of two ore more images representing said different emission conditions. When the misalignment is relative simple, e.g. predominantly shift in position, it is preferred to use variables relating to each of two coordinates of the image, e.g. shift variables. However, if the misalignment includes changes in magnifications, it is often preferred to use separate variables relating to each of the two coordinates, e.g. factor for magnification in one direction and another factor for magnification in another direction. Other equally preferred embodiments further include variables relating to both directions, e.g. variables reflecting shift and/or magnification which is determined on the position in the image. Typically, the transformation is substantially a shifting transformation, preferably where the transformation can be expressed as shift of a defined number of pixels in horizontal and/or vertical direction of the image. The degree of shifting in the shifting transformation is substantially dependent on the position in the image, preferably where horizontal and/or vertical shift is defined as a constant shift and variable shift determined as a fraction of the index of pixel of the image. The degree of shifting in horizontal and/or vertical direction is expressed as a polynomial function of the index of pixel of the image.

In yet another embodiment of the invention, a controlling unit to move the sample plane/sample holder to a predetermined position relative to field of view of the detection unit is used.

In one embodiment of the invention, the excitation light unit and the detection unit are placed on either side of the sample plane. However, in yet another embodiment of the invention, the excitation light unit and the detection unit are placed on same side of the sample plane.

In another embodiment of the invention, a processor is coupled to the detection unit to receive signal data of the fluorescence signal from the detection unit, to process the signal data, correlate the signal data to a parameter to be assessed, and assess the parameter. The apparatus further includes a means for controlling acquisition of at least two images of the same volume of the sample, wherein information from said two images represents different spectral wavelenghts.

In yet another embodiment of the invention, compensation for variable thickness of a sample holder containing a liquid sample is provided, preferably when the thickness of the sample has influence on the result of the analysis being performed, such as the determination of the number of particles per volume of sample. This is done by applying an insignia to the sample holder, or a part attached to the sample holder, or by in any form to correlate information concerning the physical dimensions of the sample holder to each measurement taken from the sample in the sample holder. In particular, when measuring at two or more separate, or partially separate positions in the sample holder, it is preferred that the differences in the thickness at the separate positions may be taken into consideration.

When determining the number of particles per volume of sample, it is necessary to determine the volume of sample analysed. Therefore, several embodiments of the present invention include means to register information and/or determining properties concerning at least one dimension of the sample holder, preferably the thickness of the sample in the sample holder in the direction facing the detector. The registration of information concerning thickness preferably involves reading an insignia reflecting a predetermination of the dimensional property, e.g. the thickness. Preferably said insignia can be read by one or more sensor of the apparatus, typically where said insignia is a pattern representation of information, such as binary code or barcode information. Several embodiments of the present invention allow the analysis of two or more segments of the sample holder, preferably when the purpose is to increase the total volume of analysed and/or to obtain a better representation of the sample being analysed, then preferably the insignia reflects physical dimension of said two or more segments of the sample holder. Further embodiments of the present invention include means for determining physical dimension of the sample holder, preferably where it is possible to perform said determination at one or more predetermined position(s) of the sample holder. Several preferred embodiments of the present invention read insignia and/or determine physical dimension using a first insignia detector, preferably the first insignia detector is same as the detector that is used for detecting images of the sample for the purpose of particle analysis. Preferably the at least one registered or determined parameter has a minimum graduation, and further where the steps of the graduation are 10% or less, when expressed as a fraction of a typical value of said parameter, preferably 8% or lesser, more preferably 6% or lesser, more preferably 4% or lesser, more preferably 2% or lesser. In several preferred embodiments said graduation is in equal steps, while in other equally preferred embodiments the graduation is in substantially unequal steps, such as when a step size is substantially equal in relative size, relative to said parameter.

In another embodiment of the present invention, a means capable of determining the type of sample holder that contains the sample being analysed is provided. Preferably, said determination is performed by reading an insignia identifying type of said sample holder and/or by detecting shape, size or other physical property of said sample holder. Preferably where said detection is preformed using a second insignia detector, preferably said second insignia detector is same as the detector that is used for detecting images of the sample for the purpose of particle analysis.

In another embodiment of the invention, a sample holder, being adapted to hold two or more different types of sample devices, without little or no adaptation, is provided. One of said sample devices is a traditional microscopy slide, or a haemocytometer chamber, such as a Büchner chamber. Preferably, the different sample devices are placed on or in a sample device holder, preferably where the sample device holder is movable, and the movement of said sample device holder is controlled by controlling means, which is capable of directing the sample device holder in accordance with the type of sample device used.

In another embodiment of the invention, the sample holder is controlled by a controlling unit, where the detection unit is used to monitor or sense one or more information concerning the sample being analysed and/or sample device used. Preferably, the information being sensed is information identifying the particles in the sample or properties of the particles in the sample and/or the sample holder or the properties of the sample holder. Preferably the controlling unit moves the sample holder to one or more predetermined position(s) relative to the field of view of the detection unit, thereby allowing the sensing of one or more information. In preferred embodiments of the present invention, information being sensed is stationary information, that is, information which does not change during the process of analysis, for example, the reading of an insignia, which represents a predetermined dimensional property of the sample holder. While, in other embodiments, the information being sensed is dynamic information, for example, movement of the sample or a part of the sample device, or indication of a chemical and/or physical property of the sample.

In another embodiment of the invention, resolution of the fluorescence signal detected by the detection unit is enhanced, where resolution of the detected fluorescence signal is the number of significantly different intervals with which the detected signal intensity is represented. The present invention allows the detection of signal with resolution which is greater than the nominal resolution of the detection unit, including electrical detecting means, by recording two or more images of the sample where substantially only differences represented in the two or more images is signal sensitivity, preferably obtained by varying exposure time and/or electrical amplification of collected signal, and subsequently combining the two or more images to a one or more image in a manner which represents the image of the sample with a greater image resolution than each of the two or more collected images. Therefore, the resolution in the detected signals is enhanced by providing different signal sensitivity in the at least two images.

One aspect of the present invention relates to a system for the assessment of particles, where the assessment comprises two or more individual tasks, where the tasks are performed in a predetermined manner and where the predetermined manner comprises a number of instructions. Preferably the instructions can be combined in a flexible manner allowing the system to be adapted to perform two or more different types of assessment of particles, where difference in type preferably reflect difference in property such as timing, excitation or emission wavelength selection.

One aspect of the present invention relates to the apparatus comprising methods for storing collected images together with identification of the sample being analysed and method of operation of the image recording system. The stored images may be arranged in a database, which allows data retrieval for the generation of reports and/or selection of one or more collected images on the bases of one or more properties.

In yet another embodiment of the invention, the sample device, which may be a vial cassette, of the described apparatus facilitates the determination of viability of cell suspensions from a wide range of cultured and primary cells, by measuring cell counts (total and non-viable) per volume.

In order to determine the viability of cells, sample of cell suspension is drawn into the sample device by pressing the piston. The inside of the sample device is coated with the fluorescent dyes Acridine Orange and 4,6-diamino-2-phenylindole (DAPI)/substituted variance of DAPI to a final concentration of 2.5 µg/mL for both AO and DAPI/substituted variance of DAPI. AO stains the entire population of cells and DAPI/substituted variance of DAPI the non-viable cells. The sample device is placed in the apparatus where the cell counts and viability are determined.

The combination of acridine orange and DAPI is suitable for determination of the viability of cells and tissues as the two DNA dyes does not show spectral overlap under any circumstances. In one method of analysis, the cells in a suspension are incubated with the two fluorescent dyes. Acridine orange permeates all cells in the population, whereas DAPI only penetrates cells with damaged membranes. Cells labeled with DAPI are detected by UV excitation and measuring blue light, whereas acridine orange labeled cells are detected by blue light excitation and measuring the emitted green light. In this manner an absolute count of cells and percent viability can be obtained from the data. Additionally, detection of the red light emitted by acridine orange may give further information about the cell status, vitality and integrity.

In other embodiments of the invention, other stains of Acridine such as 3,6-diamino acridine hydrochloride, 6,9-diamino-2-ethoxy-acridine lactate, quinacrine dihydrochloride, bis-N-methylacridinium nitrate, 10-dodecylacridine orange bromide, quinacrine mustard dihydrochloride, acriflavine hydrochloride, and 9-isothiocyanato-10-methyl acridinium triflate, and 4,6-diamion-2-phenylindole (DAPI) dye/substituted variance of DAPI to a combined concentration of 2.5 µg/mL may also be used.

In yet another aspect of the invention, a method for detecting viability of a test cell is provided using the apparatus of above description. The method comprising mixing the test cell with 4,6-diamion-2-phenylindole (DAPI) dye/or substituted variance of DAPI; allowing staining of cells for a time period of at the most 60 minutes, such as 30 minutes, such as 20 minutes, such as at most 10 minutes; obtaining a stained cell sample, wherein only non-viable cell is stained; exposing the stained test cell to an excitation light; detecting a fluorescence signal from the stained test cell; and processing the fluorescence signal to identify whether the test cell is non-viable.

In another embodiment of the invention, the test cell may also include a plurality of cells. The cell count and non-viability of the plurality of cells are identified by using 4,6-diamion-2-phenylindole (DAPI) dye/or substituted variance of DAPI. The test cell is selected from a cultured cell and primary cell. The test cell is selected from a mammalian cell line, mammalian cell line in suspension, insect cell line, such as *Drosophila melanogaster* Schneider-2, human embryonic cell line, primary cell and human blood cell. The test cell is prepared under a controlled environment, as exemplified in Material and Method section in the examples.

In yet another embodiment of the invention, Acridine Orange dye is mixed with 4,6-diamion-2-phenylindole (DAPI) dye/substituted variance of DAPI to a combined concentration of 2.5 μg/mL. A sample device in which the test sample is injected/loaded is coated with a combination of the AO dye and DAPI dye/substituted variance of DAPI. The Acridine Orange dye stains both viable test cell and non-viable test cell.

In yet another embodiment of the invention, the test cells are injected/loaded into the sample device using a piston.

The excitation light is from a source selected from a thermal light source, such as a halogen lamp, or a gas lamp such as a xenon lamp, a light emitting diode, a laser or a laser diode or any other light source as described in the apparatus above.

The fluorescence signal is processed by analyzing the fluorescence signal for number of counts of non-viable cells in the cells.

This method is performed using an apparatus that labels a test cell. The apparatus comprises of a sample device coated at least partly with 4,6-diamion-2-phenylindole (DAPI) dye/substituted variance of DAPI, wherein the DAPI/substituted variance of DAPI only stains a non-viable cell; a test cell injecting unit to load the test cell into the sample device; an excitation unit to expose the injected test cell to an excitation light; a detection unit to detect a fluorescence signal emitted from the loaded test cell; and a processor to process the fluorescence signal to assess whether the test is non-viable.

In yet another embodiment of the invention, a method for providing information about a cell is provided using the above described illumination apparatus and detection apparatus. The method comprises of transfecting the cell with a fluorescent protein or fluorescently labelled nucleic acid; adding a thiol-reacting molecule to the transfected cell to obtain a cell solution; exposing the cell solution to an excitation light; detecting an emission light from the cell solution; and processing the emission light to obtain the information about the cell.

The method presented here uses fluorescent proteins or fluorescently labeled nucleic acid in combination with a thiol-reacting molecule, such as maleimides (e.g. DACM) and a cell-impermable DNA stain (e.g. propidium iodide) for monitoring transfection efficiency and at the same providing information about viability of the cell population and cytotoxicity levels.

The information usually includes transfection efficiency, cell viability and cytotoxicity level, i.e. detecting non-viable cells.

The cell is selected from a cultured cell and primary cell. The cell is selected from a from a mammalian cell line, mammalian cell line in suspension, insect cell line, such as *Drosophila melanogaster* Schneider-2, human embryonic cell line, primary cell and human blood cell.

The method further comprises of mixing a cell-impermable DNA stain. The cell-impermeable DNA stain may be propidium iodide, and acridine homodimer. The nucleic acid is selected from a fluorescent protein and a small interference RNA. The thiol reacting molecule is a maleimide, such as DACM.

In another embodiment of the invention, the cell includes a plurality of cells. Also, the information about plurality of cells is identified by using a combination of a fluorescent protein or fluorescently labelled nucleic acid and a thiol-reacting molecule.

The excitation light is from a source selected from a thermal light source, such as a halogen lamp, or a gas lamp such as a xenon lamp, a light emitting diode, a laser or a laser diode or any other light source described in the previous sections.

In several embodiments of the present invention, the excitation light is a green light and the emission light is a red light for determining a non-viable cell, when propidium iodide is used as a cell impermeable DNA stain; and the excitation light is a blue light and the emission light is a green light for determining a non-viable cell, when acridine homodimer is used as a cell impermeable DNA stain.

In several embodiments of the present invention, the cell expressing BFP emits a blue light when it is excited with a UV or violet light; the cell expressing CFP emits a cyan light when it is excited with a violet or blue light; the cell expressing GFP emits a green light when it is excited with a blue light; the cell expressing YFP emits a yellow light when it is excited with a blue or green light; the cell expressing dsRed or variants of this emits a red light when it is excited with a green light; the cell harbouring siRNA emits a blue light when it is excited with a UV or violet light; the cell harbouring siRNA emits a cyan light when it is excited with a violet or blue light; the cell harbouring siRNA emits a green light when it is excited with a blue light; the cell harbouring siRNA emits a yellow light when it is excited with a blue or green light; and the cell harbouring siRNA emits a red light when it is excited with a green light.

The detecting comprises receiving the emission light at atleast one detector and the processing comprises of analyzing the emission light for determining transfection efficiency, cell viability and cytotoxicity level.

The above method is implemented using an apparatus, which is used to determine information about a cell. The apparatus includes a transfecting unit to transfect the cell with a fluorescent protein or fluorescently labelled nucleic acid; a mixing unit to add a thiol-reacting molecule to the transfected cell to obtain a cell solution; an excitation unit to expose the cell solution to an excitation light; a detection unit to detect an emission light from the cell solution; and a processor to process the emission light to obtain the information about the cell.

The apparatus and method of the present invention was used for analyzing particles in a sample. The invention provides a simple, rapid and flexible device for analyzing cells at low magnification, hereunder characterizing cells, detecting cells, counting cells as well as determining the viability, motility, metabolic activity, metabolite quantitation, cell division, proliferation, health, stress level, apoptosis, necrosis, other state of condition, or morphology of cells. Several examples of such analyses are presented below for better understanding of the present invention:

Example 1

Focusing of Illumination Light Using Traditional Apparatus (Refer FIG. 1)

FIG. 1A shows an imaginary light source, showing substantial structure in its light emitting elements (101), comprising 4 square regions emitting light evenly, separated and surrounded by passive elements (102), emitting no detectable light. The light source measures 1×1 mm, and the angular emission is from +40 to −40 deg.

FIG. 1B shows an arrangement, simulating the use of a light source (103, identical to item 101) for the illumination of a sample material. The figure shows a Biconvex Aspheric Lens (104), which has a focal length f=8.5 mm and a diameter D=12 mm (one such available from Melles Griot LAG000). Further the system comprises a filter element (105) typically used in fluorescence analysis for the elimination of light at wavelengths where emission is expected. Finally the system comprises a Plano Convex Lens (106), which has a focal length f=12 mm and a diameter D=12 mm (one such available from Edmund Optics part no 45084) and finally the sample material (107) which is to be illuminated.

FIG. 1B shows a number of randomly selected rays and illustrates the path of these rays through the system.

FIG. 1C shows a simulated image of the light source, as it would appear on the sample material. FIG. 1C shows strong similarity with the light source illustrated in FIG. 1A, where the emittance structure is easily identified. If suppression or elimination of the structure is wanted it becomes necessary to use a diffusing means, e.g. by using a diffuser. This would affect the size of image and cause "blurring" resulting in broderning of the illumination and thus loss of effective light and/or decreased homogeneity of the illumination light.

Example 2

Figure 2:
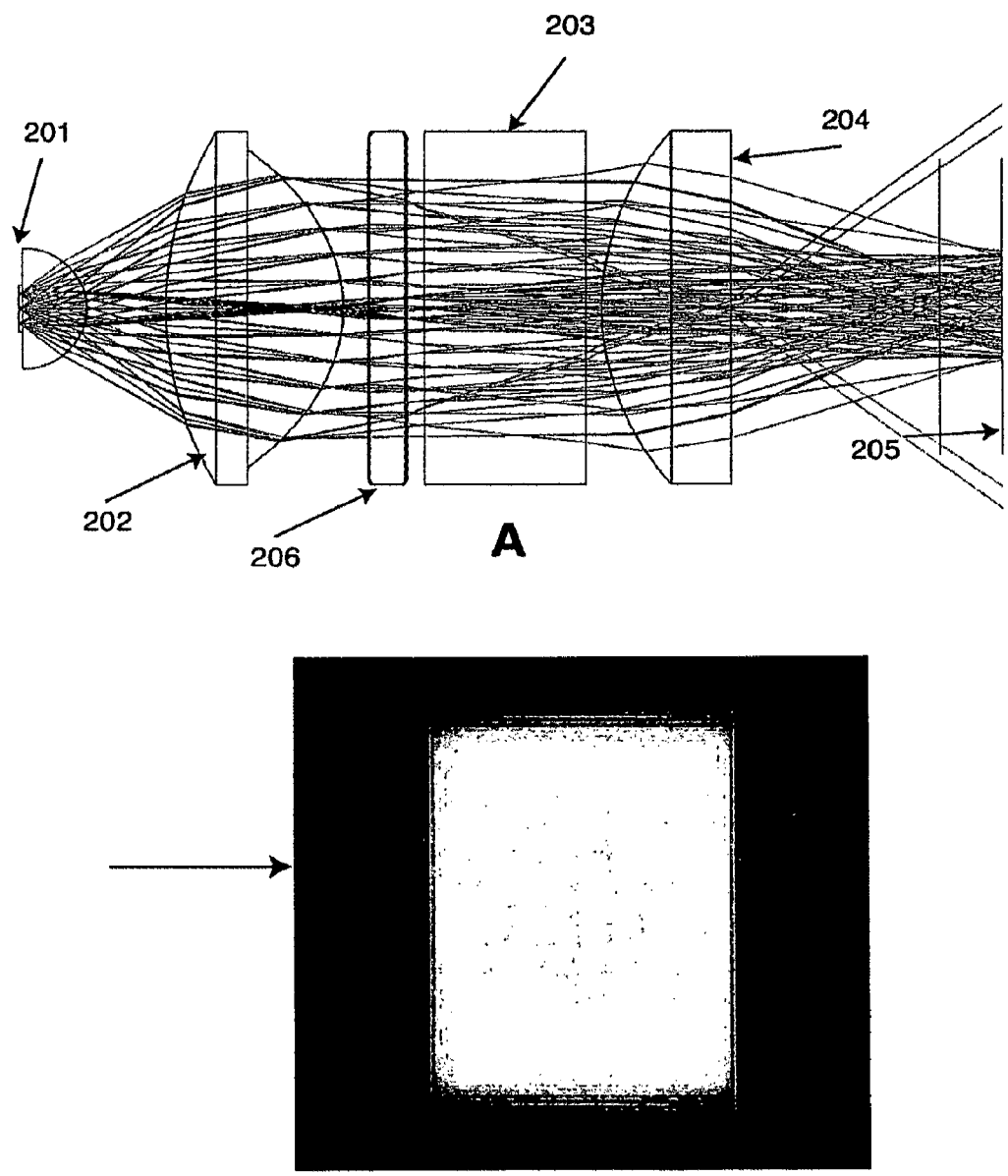
FIG. 2 illustrates system for the illumination of a sample material using a micro lens array.

Focusing of Illumination Light by Micro Lens Array (Refer FIG. 2)

FIG. 2A shows an arrangement, simulating illumination of a sample material, similar to the system in Example 1, with the addition of a micro lens array (206). The system contains a light source (201) identical to the one in FIG. 1A, biconvex aspheric lens (202), a filter element (203), a plano convex lens (204) and finally the sample material to be illuminated (205).

The micro lens array (206) is 12 mm in diameter, and the circumscribed square (12 by 12 mm) is divided into 60×44 rectangular adjacent symmetrical biconvex lens elements with a thickness of 1.191 mm and lens radii of 0.4 mm and −0.4 mm respectively, each individual lens element is generating a small image of the light source and when all individual images are superimposed on the sample a rectangular shaped with homogeny illumination is present.

The system was subjected to simulation identical to the one in Example 1 and the result is illustrated in FIG. 2B, which shows the illumination of the sample material. FIG. 2B shows that the structure of the light source is substantially eliminated, substantially without loss of illumination efficiency due to broadening of the illumination. These properties are highly preferred when performing photoluminecent analysis, such as fluorescence analysis.

Example 3

Figure 3:
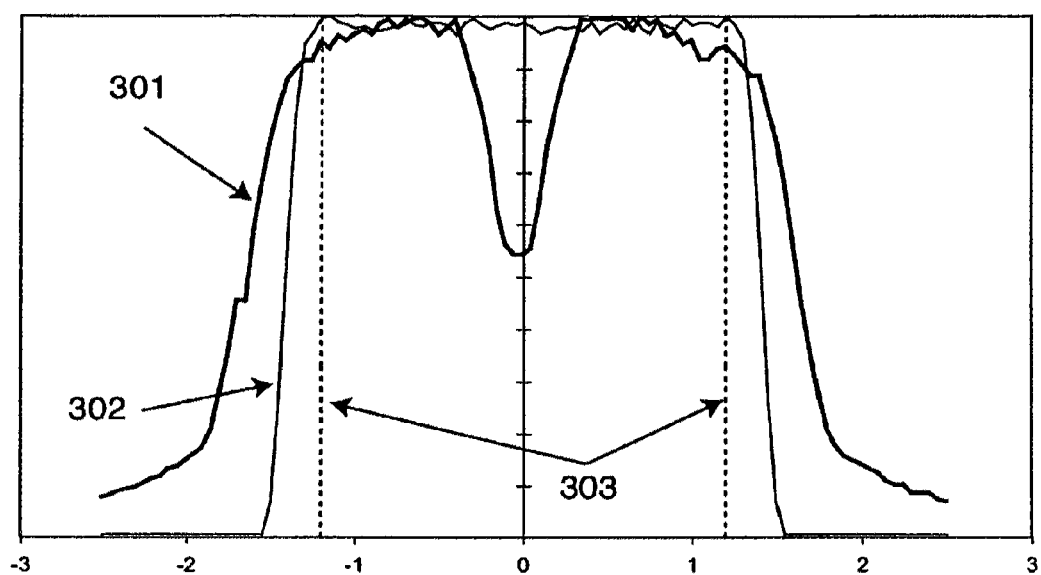
FIG. 3 illustrates the comparison of two methods for the illumination of sample material.

Comparison of Illumination (Refer FIG. 3)

FIG. 3 shows a graph, illustrating the difference of simple illumination and illumination according to the present invention, when using a light source having substantial illumination structure. The comparison is based on the results of Examples 1 and 2 as described above.

The graph in FIG. 3 shows intensity of the illumination as found in Examples 1 and 2 and indicated in FIGS. 1C and 2B, along a horizontal line indicated by the arrows in the figures.

The illumination as found in Example 1 is represented by the line 301, while the illumination as found in Example 2 is represented by the line 302. The lines 303 represent the boundaries of the illumination as defined by magnification of the optical system.

The graph illustrates that line 302 has less spread outside the boundaries 303 than does line 301, which will give greater illumination efficiency. Further the variation in line 302 within the boundaries 303 is considerably less than the variation in line 301, both with respect to the structure in the emittance of the light source, present as a significant drop in illumination in the centre and as significant drop-off in intensity towards the edges of the boundaries.

Example 4

Figure 4:
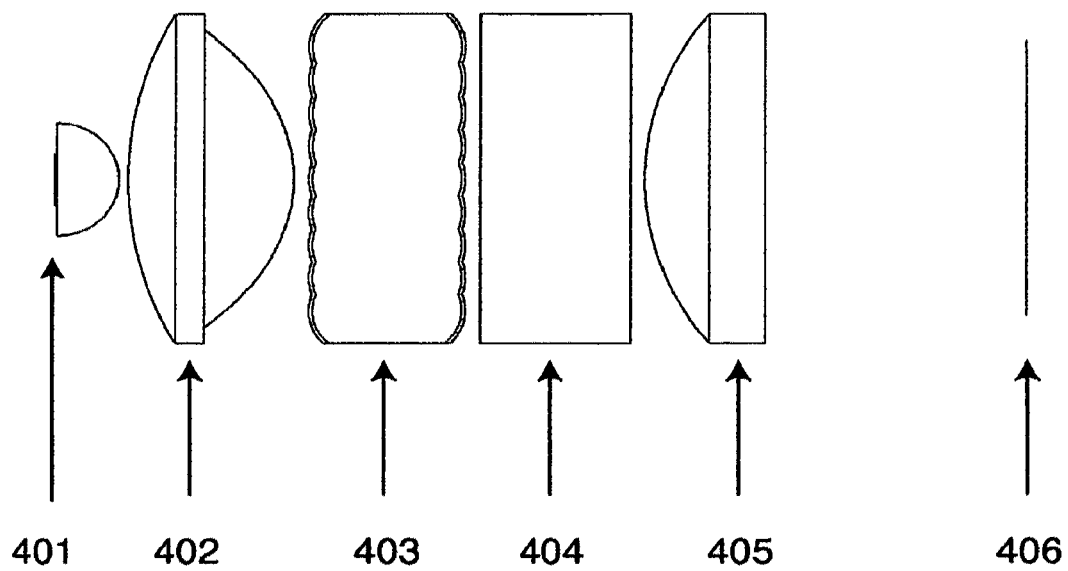
FIG. 4 illustrates an implementation according to the present invention.
Figure 4:
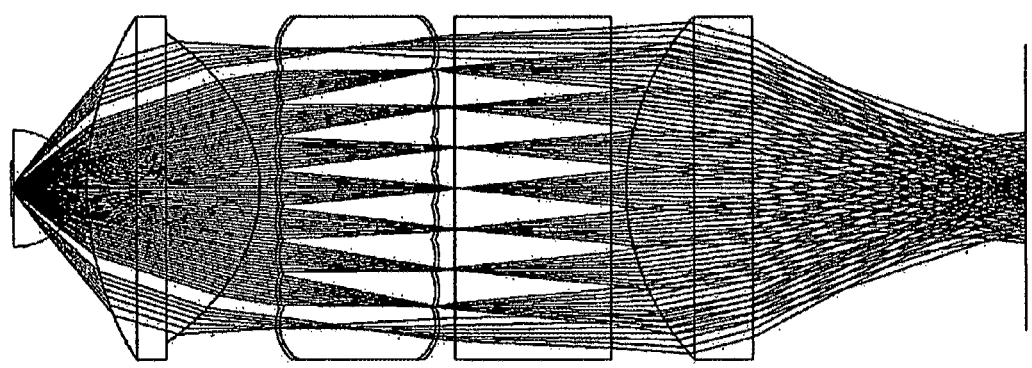

Implementation According to the Present Invention (Refer FIG. 4)

FIG. 4 shows an implementation according to the present invention. It illustrates an optical system, comprising a light source (401), for instance ML101J17-01 (Mitsubishi, Japan), LZ1-00xx05 or LZ1-00xx03 (LedEngin, USA), specifically the selection of light source depends on the desired wavelength region and intensity. Further it comprises a collimating lens (402), e.g. LAG000 (Melles Griot, USA), an array of micro lenses (403), e.g. double sided lens array element, a spectral filter means (404), typically interference and/or absorbing filters, in fluorescence analysis the filter is termed excitation filter, and finally a focusing component (405), e.g. a PCX og DCX lens with effective focal length of between 2 and 20 mm, where the effect of changing the focal length affects the size of the region illuminated by the light source. Finally the illustration shows the illumination plane (406), onto which it is desired to project a relatively homogeneous light from the light source, e.g. illumination region, preferably with relatively high illumination efficiency.

FIG. 4B shows the implementation according to the present invention, where simulated rays of light are drawn, demonstrating the optical operation of the system.

Example 5

Figure 5:
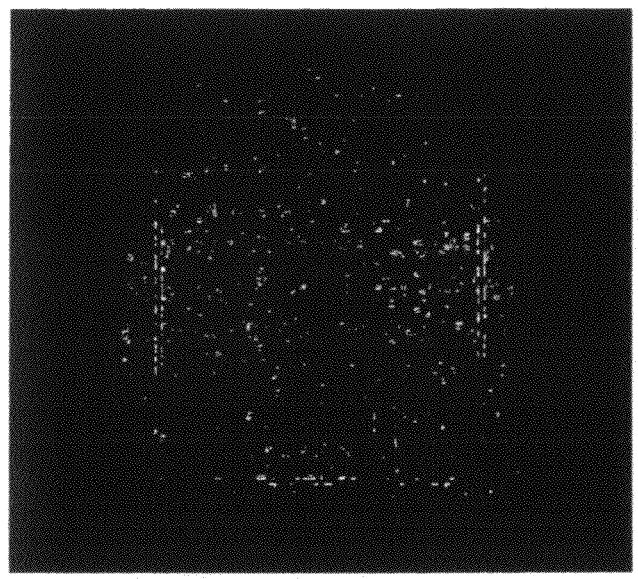
FIG. 5 illustrates size of illumination region according to the present invention.
Figure 5:
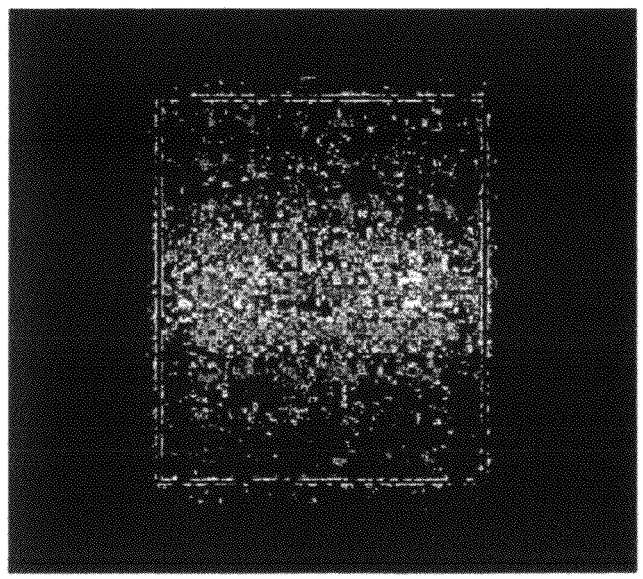

Adaptation of Illumination Region (Refer FIG. 5)

FIG. 5 shows the illumination of illumination means according to the present invention. The difference between FIGS. 5A and 5B shows the effect of reducing the focal length of the focusing element (405 in FIG. 4), thus affecting the effective size of the illumination region.

Example 6

Figure 6:
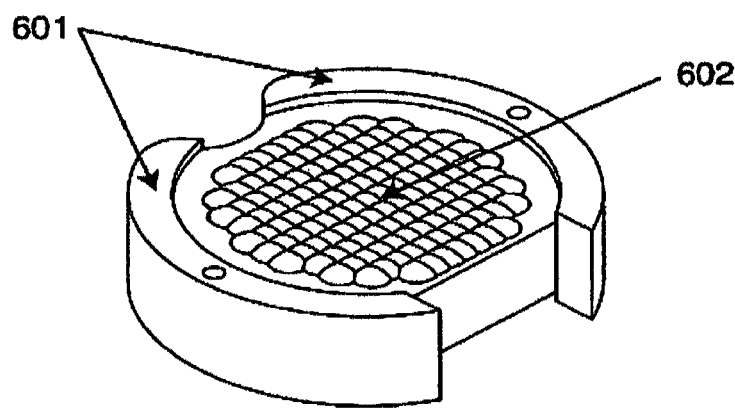
FIG. 6 illustrates a micro lens array element according to the present invention.
Figure 6:
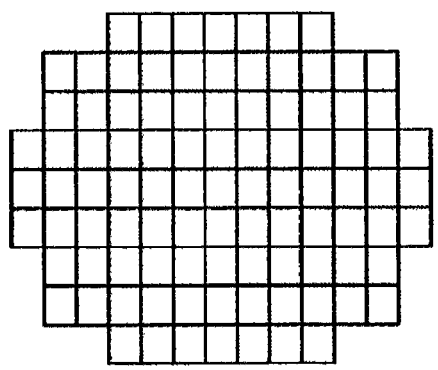

Element of Micro Lenses (Refer FIG. 6)

FIG. 6 shows a micro lens array element according to the present invention. The element shown in FIG. 6A is a thermal plastic item, comprising means for arranging and fixing the element (601), here on the form of a rim, and two arrays of micro lenses (602), of which the array on the bottom is not shown.

Each of the micro lens arrays consists of a a number of 1.2×0.9 mm lenses of 1.7 mm radius, separated by about 5 mm, which is the thickness of the micro lens element. The pattern of the micro lenses, shown in FIG. 6B, is a 13 by 9 grid, which has been roughly shaped in a circular fashion, preferably similar to the shape of the beam of light, to reduce physical size, by removing 5 lenses from each corner.

Example 7

Figure 7:
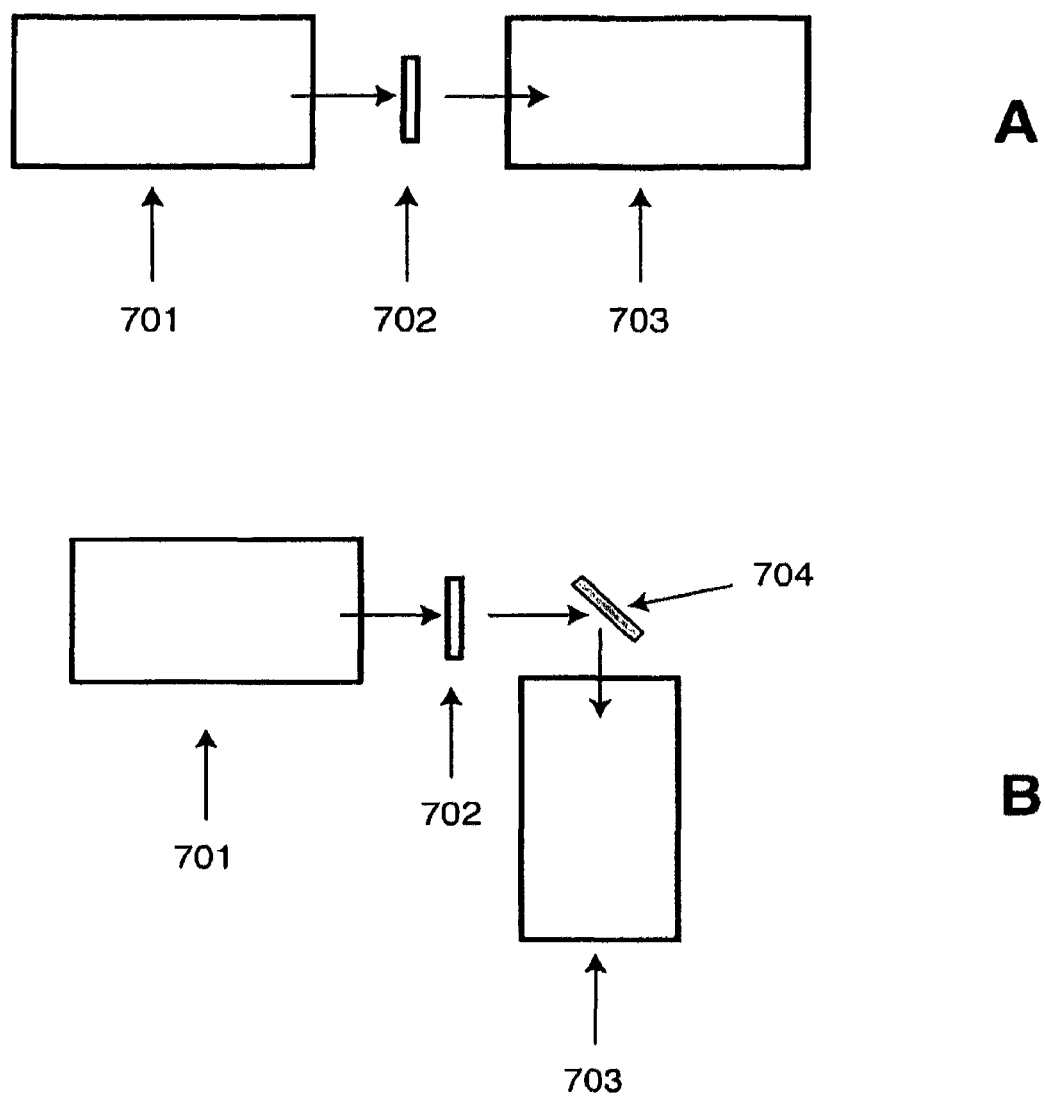
FIG. 7 illustrates in A) an arrangement of the apparatus where the units are arranged on, or substantially on the optical axis of a photoluminescent imaging system, preferably in an arrangement where the illumination light is directed directly towards a detector unit of an imaging system, and in B) an arrangement where the units are arranged substantially off the optical axis of a photoluminescent imaging system, preferably in an arrangement that includes a dichroic mirror reflecting the illumination light onto the sample along the axis of an imaging system.
Figure 8A:
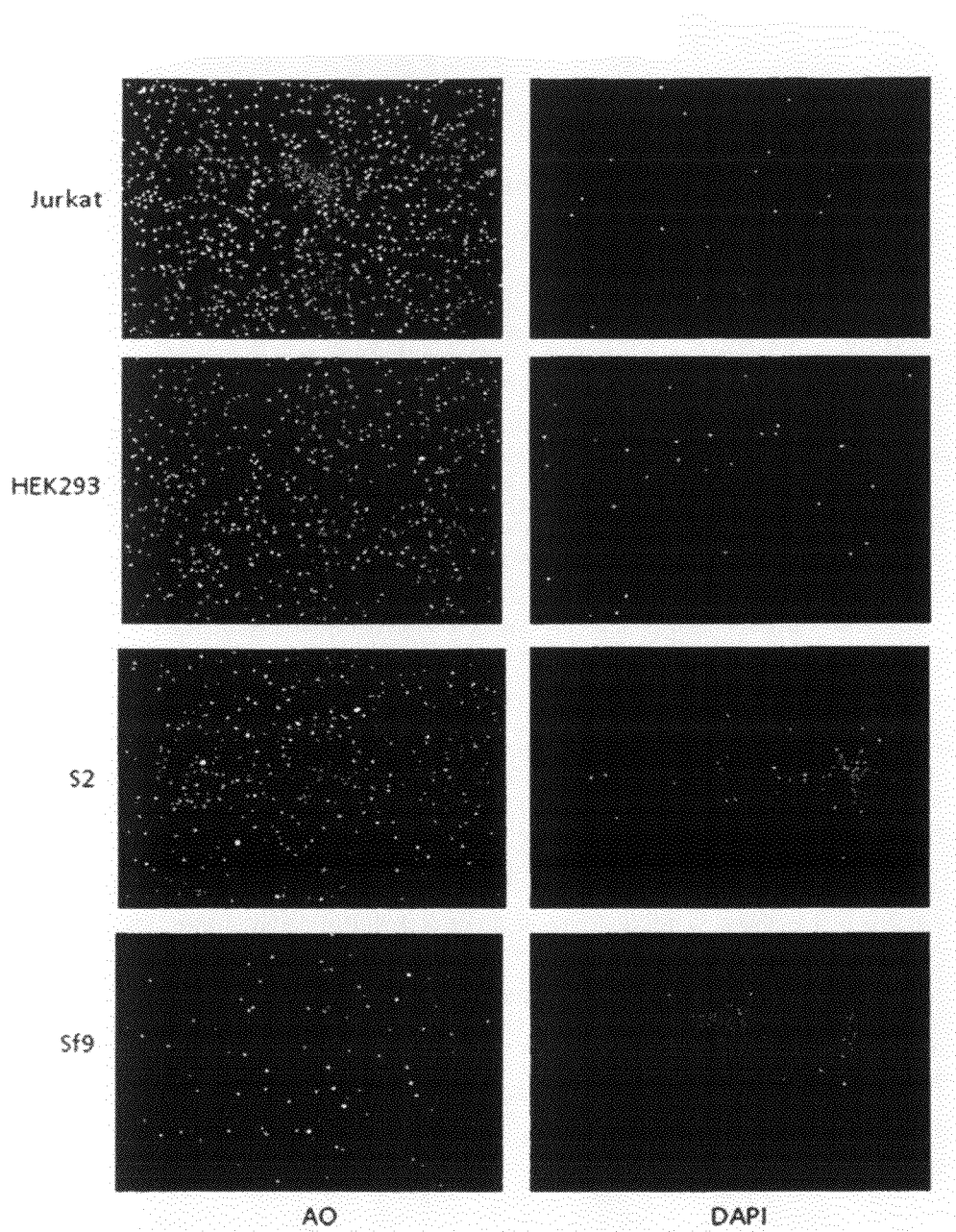
FIG. 8 illustrates in A) images of Jurkat, HEK293, S2 and Sf9 cell cultures, composed by the apparatus (2× magnification). Each panel shows image of the same cells: left; AO, right; DAPI; and B) illustrates images of Jurkat cell cultures, composed by the apparatus (2× magnification). Each panel shows image of the same cells: upper; AO, middle; DAPI, lower; superimposition of the two images.
Figure 8B:
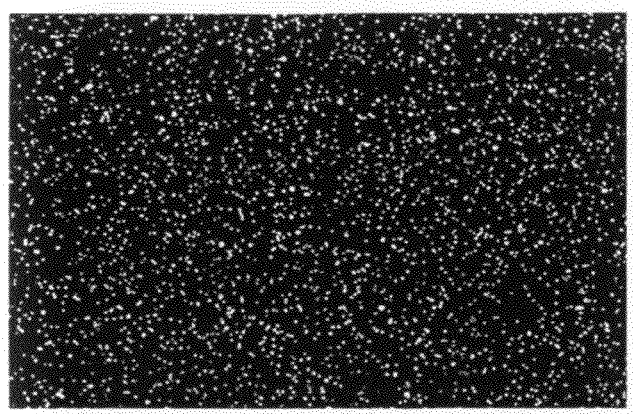
Figure 8B:
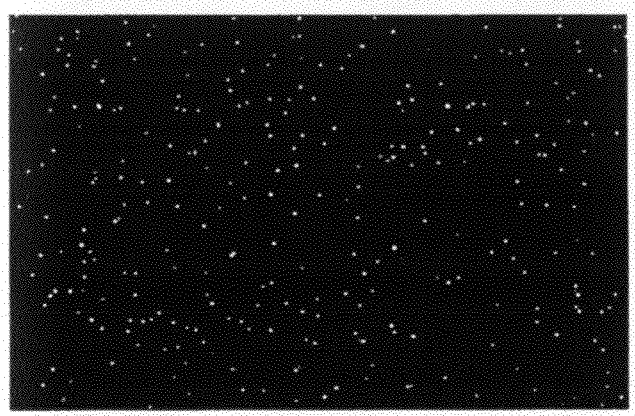
Figure 8B:
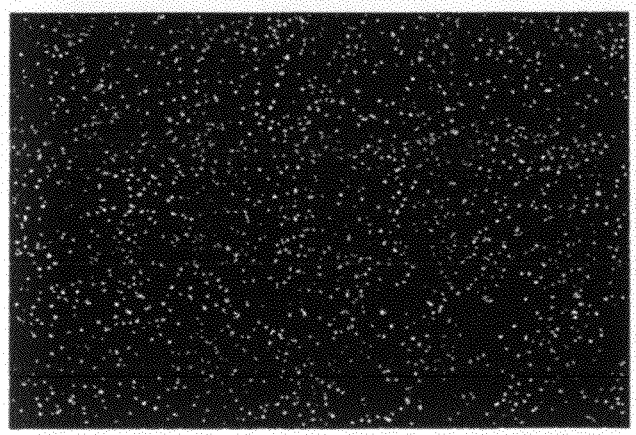

Arrangement of Optical Module (Refer FIG. 7)

A typical embodiment according to present invention includes two or more optical modules and FIG. 7 shows the arrangement of these modules. The modules are illumination module (701), sample or sample compartment (702), detection module (703) and an optical mirror (704).

FIG. 7A shows a preferred embodiment comprising an illumination, sample and detection module, where all modules are arranged on a parallel axes relative to each other. The illumination module, typically comprising of a light source, focusing optic and wavelength separation means (these items not shown in the figure) illuminates light onto the sample compartment, where the sample it typically arranged in a perpendicular orientation relative to the main axes of light emitted from the modulation module. Typically signals from the sample compartment are emitted in all directions from but a fraction of these signals are collected by the detection module, which in this arrangement is on, or substantially on, the same axes as the illumination module and the sample compartment.

FIG. 7B shows another equally preferred embodiment of the present invention, where signals from the sample compartment are directed towards the detection module by an optical mirror. This embodiment allows the detection module to be situation outside the axes formed between the illumination and sample compartment modules, such as illustrated in FIG. 7B, where the detector module is in a perpendicular arrangement.

As FIG. 7 only shows the general orientation of the different modules, and not the position of different elements, it is obvious to a person skilled in the art, that when including an optical mirror to direct the light off the optical axis, it can often be advantageous to include an optical component of the detection module, such as one or more lens(es) between the sample compartment module and the optical mirror. Typically the effect of such arrangement would be to assure a more parallel nature of the light emitted from the sample compartment, detected in the detection module, which can render more homogeneous reaction of the light to a wavelength dependent property, such as filtration, and/or to increase the effective aperture of the detection module, by placing a collecting optic close to the image.

Embodiments of the present invention include two or more detection modules, for instance by combining the arrangement shown in FIGS. 7A and B. This is typically done by including an optical mirror with wavelength dependent reflectance properties, such that reflectance/transmittance properties are substantially different for different wavelengths. Such embodiments allow simultaneous detection of two or more optical properties of the sample in the sample compartment module.

Example 8

Figure 9:
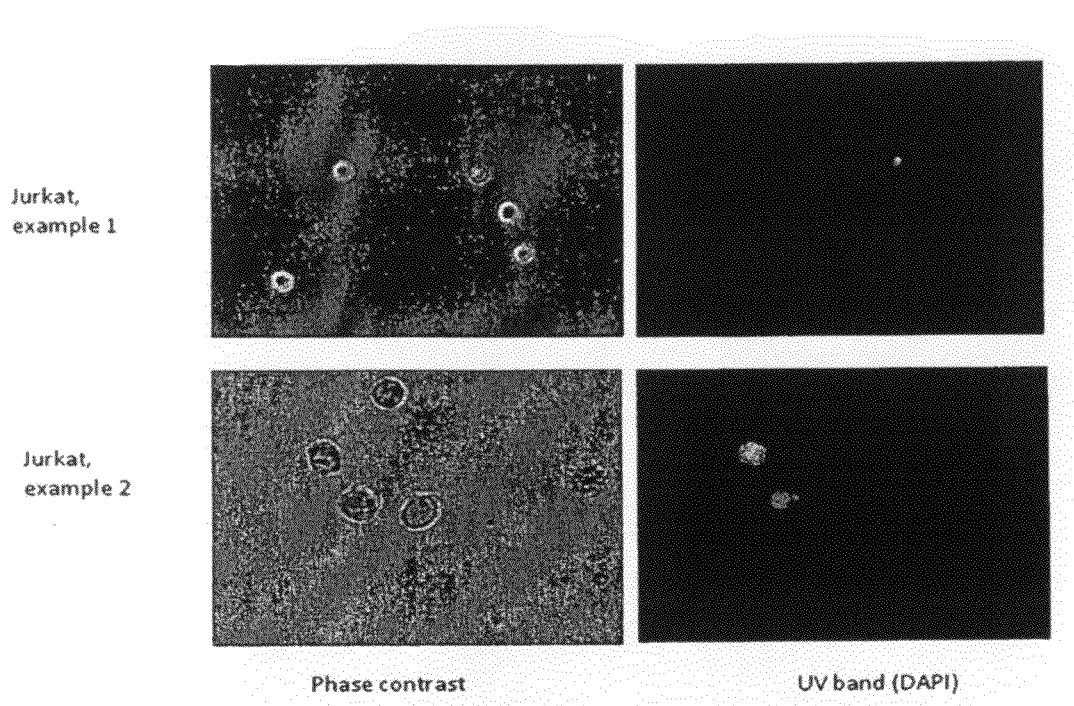
FIG. 9 illustrates fluorescent microscopy of Jurkat cells stained with DAPI and micrographed at 40× magnification using a UV band pass filter cube. Each panel shows the following images of the same cells: left; phase contrast, right; DAPI.
Figure 10:
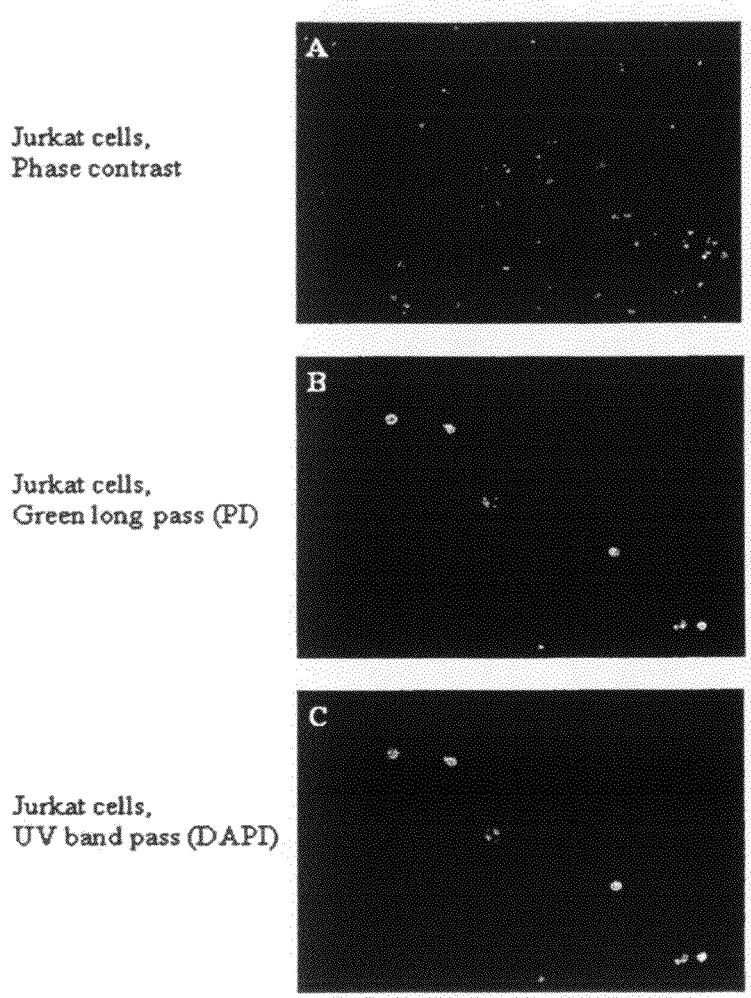
FIG. 10 illustrates fluorescent microscopy of Jurkat cells micrographed at 20× magnification. A) phase contrast. B) PI stained cells (green longpass filter cube) C) DAPI stained cells (UV bandpass filter cube)

Cell Count and Viability of Cells in Suspension; Jurkat (JM) Cells (a T Lymphocyte Cell Line) (Refer FIGS. 8, 9 and 10)

Materials and Methods.

Jurkat (JM) cells were cultivated at 37° C. in a humidified air atmosphere with 5% $CO_2$ in RPMI (Invitrogen, #61870) supplemented with 10% heat-inactivated fetal bovine serum (Invitrogen, #10108-165). Jurkat cells (cell density $1.4 \times 10^6$, 98% viability was determined using the apparatus loaded into a sample device, containing the fluorescent stains Acridine Orange (AO) and 4,6-diamino-2-phenyindole (DAPI). The sample device was placed in the apparatus and the cells were counted and investigated using the apparatus. To show that DAPI functions to stain dead cells and dead cells only, propidium iodide (PI) staining of cells was used together with DAPI. PI is membrane impermeant and thus excluded from viable cells. Stained cells were also investigated using an Olympus IX50 fluorescent microscope. Images were captured using a Lumenera CCD camera and in-house developed software. DAPI fluorescence was detected using a U-MNUA2 (UV band pass, 330-385 nm) filter cube (Olympus) and PI fluorescence was detected using a U-MWG2 (green longpass) filter cube (Olympus).

Results.

Both AO and DAPI stain the Jurkat cells immediately, staining the entire population and the non-viable cells, respectively, whereby the viability of the cell population can be determined. Double staining using DAPI and PI showed that they stained the same cells, thus confirming that DAPI can be used as a stain for nonviable cells. However, it was observed that during incubation (more than 15 minutes) DAPI also stained a part of the PI negative population. Moreover, observing the cells at phase contrast and under a UV filter in the fluorescent microscope, detecting the DAPI stained cells, it was clear that the cells which appeared dead at phase contrast were also found to be DAPI positive and thus dead.

Example 9

Cell Count and Viability of Adherent Cells; HEK293 Cells (a Human Embryonic Kidney Cell Line) (Refer FIG. 8A)

Materials and Methods.

HEK293 cells were grown at 37° C. in a humidified air atmosphere with 5% $CO_2$ in DMEM (Invitrogen, #31966) supplemented with 10% heat-inactivated fetal bovine serum (Invitrogen, #10108-165). At 50% confluency cells were harvested with 0.5 mL trypsin (Invitrogen, #25300) and neutralized with 5 mL medium (DMEM+10% FCS). Cells were loaded into a sample device, containing the fluorescent stains Acridine Orange (AO) and 4,6-diamino-2-phenyindole (DAPI), and the cassette was placed in the apparatus. The cells were counted and investigated using the apparatus and in-house developed software.

Results.

As for the Jurkat cells, the HEK293 cells were immediately stained with AO and DAPI, staining the entire population and the non-viable cells, respectively, thus determining the viability of the cell population.

Example 10

Cell Count and Viability of Insect Cell Lines; S2 and Sf9 Cell Lines (Refer FIG. 8A)

*Drosophila melanogaster* Schneider line-2 (S2) cells were originally derived from late embryonic stage *Drosophila embryos*, and the Sf9 cell line was originally derived from pupal ovarian tissue of the Fall armyworm *Spodoptera frugiperda*.

Materials and Methods.

S2 and Sf9 cells were grown at 28° C. without shaking in Schneider's *Drosophila* medium (Invitrogen, #21720) and Grace's insect medium (Invitrogen, #11605), respectively, supplemented with 10% heat-inactivated fetal bovine serum (Invitrogen, #10108-165). Cells were loaded into a sample device, which was placed in the apparatus. The cells were counted and investigated using the apparatus.

Results.

As was the case for the suspension and adherent cell lines, the insect cell lines were also stained immediately with AO and DAPI in the Via1-Cassette, showing that the Via1-Cassette can also be used to measure viability in insect cells.

Example 11

Figure 11:
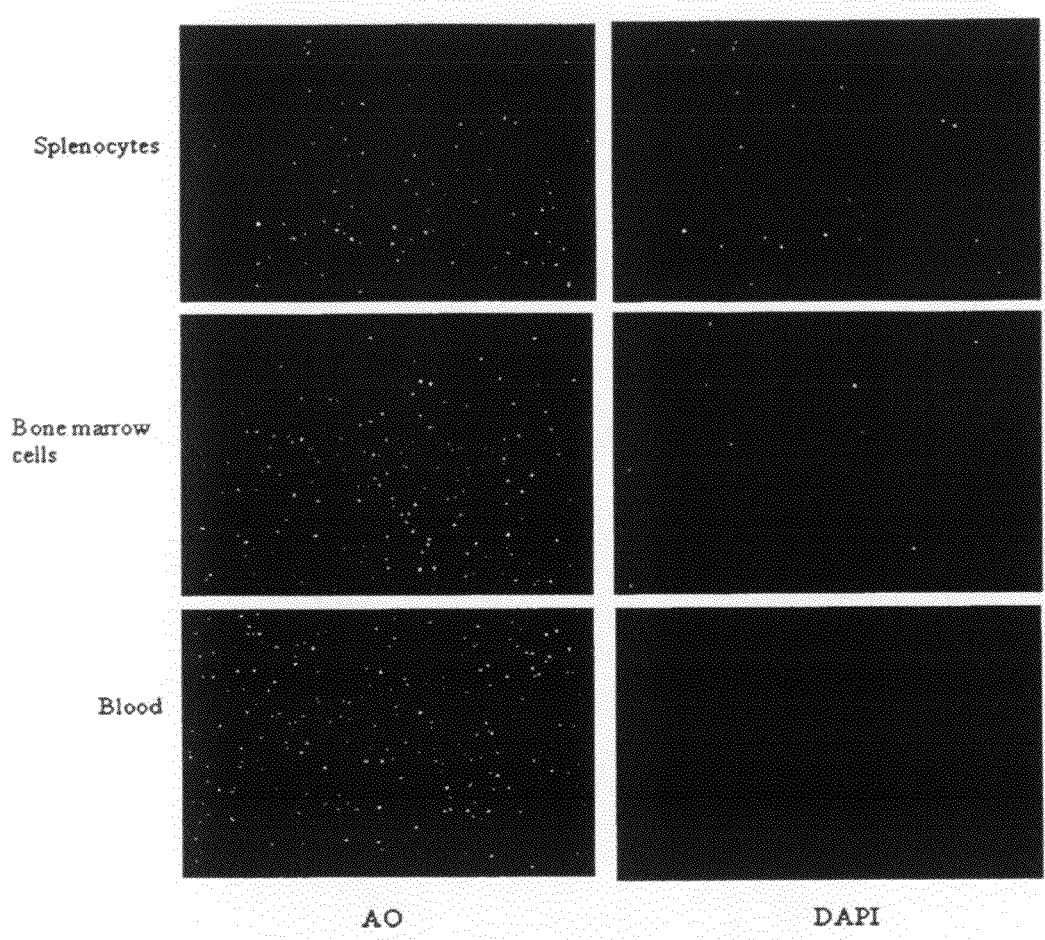
FIG. 11 illustrates images of isolated primary murine splenocytes, murine bone marrow cells and human blood cells, composed by the apparatus (2× magnification). Each panel shows the images of the same cells: left; AO, right; DAPI.

Cell Count and Viability of Primary Cells; Murine Splenocytes, Murine Bone Marrow Cells and Human Blood Cells (Refer FIG. 11)

Materials and Methods:

The spleen from a C57BL/6 mouse was placed in ice-cold PBS and gently ground using the end of a sterile syringe. The suspension was centrifuged at 300 g for 10 minutes; the pellet was resuspended in 1 mL 0.83% $NH_4Cl$ to lyse erythrocytes and was incubated for 3 minutes on ice. The cells were then added 14 mL PBS and centrifuged at 300 g for 10 minutes. The splenocytes were resuspended in RPMI (Invitrogen, #61870) supplemented with 10% heat-inactivated fetal bovine serum (Invitrogen, #10108-165), 100 U/mL penicillin and 100 µg/mL streptomycin (Invitrogen, #15140-122). The cell clumps were allowed to sediment and were removed by pipetting, and the resulting single cell suspension was used for analysis.

The bone marrow cells were harvested aseptically in the laminar flow hood. Bilateral tibia and femur were aseptically removed, freed of surrounding soft tissue, and placed in a petri dish with 10 mL 70% ethanol. After 2 minutes they were transferred to ice cold PBS. The bone marrow cavity was then flushed with 5 ml cold PBS using a 5-ml syringe with a 27-gauge needle attached, and the cells were collected from each bone. The cells were centrifuged at 300 g for 10 min, the supernatant was discarded, and cells were washed twice. After the second wash the cell pellet was resuspended in RPMI 1640 (Invitrogen, #61870) supplemented with 10% heat-inactivated fetal bovine serum (Invitrogen, #10108-165), 100 U/mL penicillin and 100 µg/mL streptomycin (Invitrogen, #15140-122).

A small sample of human venous blood was drawn from a fingertip by use of a needle. The blood sample was diluted 5 times in PBS before analysis.

A sample of each of the primary cells (murine splenocytes, murine bone marrow cells and human blood cells) was loaded into the sample device and analysed in the apparatus.

Results.

As was the case for the suspension, adherent and insect cell lines, the primary cells (murine splenocytes, murine bone marrow cells and human blood cells) were also stained immediately with AO and DAPI in the Via1-Cassette, staining the entire population and the dead population of cells, respectively. This shows that the Via1-Cassette can also be used to measure viability in primary cells.

Example 12

Figure 12:
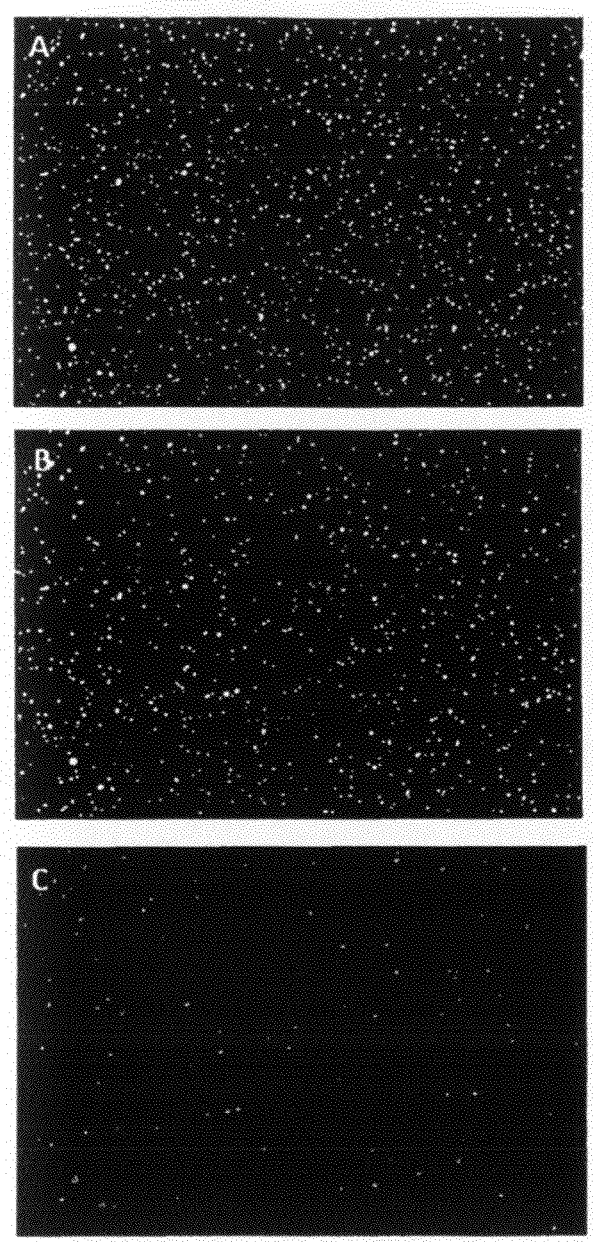
FIG. 12 illustrates in A) HEK293 cells stained with DACM are shown. B) HEK293 cells transfected with a CMV-RFP fusion are shown. C) Combination of image A and B, Colour code; Blue: DACM; Red: RFP.

Transfection Efficiency and Cell Count of Cells Expressing RFP Using DACM. (Refer FIG. 12)

HEK293 is an embryonic human kidney cell line which in this example has been transfected with a RFP (mRFP1 derived from dsRed) fused to CMV promoter; EC41. Using DACM to stain all viable cells and RFP to detect transfected cells, the ratio of transfected viable cells to all cells (the transfection efficiency) can easily be determined.

Materials and Methods.

HEK293 cells were cultivated at 37° C. in a humidified air atmosphere with 5% $CO_2$ in RPMI (Invitrogen, #61870) supplemented with 10% heat-inactivated fetal bovine serum (Invitrogen, #10108-165). 190 µL of a mixture of transfected and untransfected HEK293 EC41 cells were added 10 µL DACM (N-(7-dimethylamino-4-methyl-3-coumarinyl)-maleimide, WAKO Pure Chemical Industries, CAS no. 55145-14-7) dissolved in DMSO (200 µg DACM pr·mL DMSO) and mixed by pipetting. Cells were loaded into a NucleoCassette (not containing propidium iodide or other stains). The NucleoCassette was placed in the apparatus and the cells were counted and investigated using the apparatus.

Results.

The concentration of all viable cells (based on the cells stained by DACM, FIG. 5) was determined to be $2.4 \times 10^6$ cells pr·mL. The concentration of cells expressing RFP was determined to be $1.7 \times 10^6$ cells pr·mL and the transfection efficiency was thus found to be 71.5%.

Conclusion.

Thiol-reacting probes such as DACM can be used in assays for determining the transfection efficiency when the transfection involves fluorescent proteins.

Example 13

Figure 13:
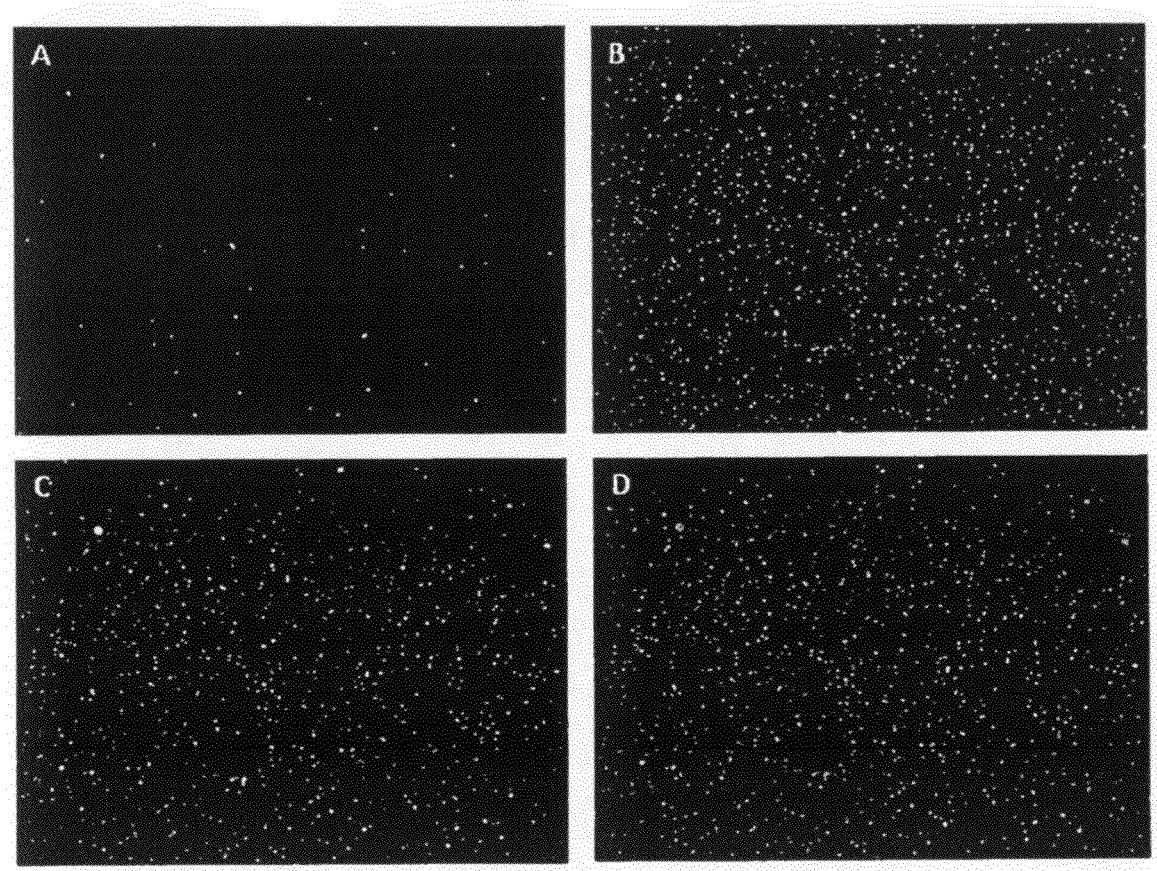
FIG. 13 illustrates in A) MCF-7 EC3 cells stained with PI B) MCF-7 EC3 cells stained with DACM C) MCF-7 EC3 cells expressing GFP D) FIGS. A, B and C combined (colour code; red PI, Blue DACM, green GFP)
Figure 14:
FIG. 14 illustrates a mixture of GFP transfected and untransfected MCF-7 cells. Colour code; red; PI (green long-pass), green; GFP (blue bandpass) and blue; DACM (UV bandpass)

Transfection Efficiency, Cell Count and Viability of Cells Expressing GFP Using DACM and PI (Refer FIG. 13 and FIG. 14)

MCF-7 is a breast cancer cell line which in this example has been transfected with a GFP fused to the CMV promoter. Using propidium iodide (PI) for staining non-viable cells, DACM for staining all viable cells and GFP to detect transfected cells, the transfection efficiency, cell viability and cell count can easily be determined.

Materials and Methods.

MCF-7 cells stably expressing GFP (MCF-7 EC3) were cultivated at 37° C. in a humidified air atmosphere with 5% $CO_2$ in RPMI (Invitrogen, #61870) supplemented with 10% heat-inactivated fetal bovine serum (Invitrogen, #10108-165). 190 µL MCF-7 EC3 cells were added 10 µL DACM (N-(7-dimethylamino-4-methyl-3-coumarinyl)-maleimide, WAKO Pure Chemical Industries, CAS no. 55145-14-7) dissolved in DMSO (200 µg DACM pr·mL DMSO) and mixed by pipetting. Cells were loaded into a NucleoCassette containing the DNA stain propidium iodide (PI). PI is membrane impermeant and is therefore excluded from viable cells. The NucleoCassette was placed in the apparatus and the cells were counted and investigated using the apparatus. The cells were also investigated using an Olympus IX50 fluorescent microscope, and images were captured using a Lumenera CCD camera and in-house developed software. PI, DACM and GFP fluorescence were detected using, respectively, U-MWG2 (green long pass: 510-550 nm), U-MNUA2 (UV band pass, 330-385 nm) and (blue long pass) filter cubes (Olympus).

Results.

A low fraction of the cells were stained by PI (FIG. 6A) and the apparatus determined the concentration of non-viable cells to be $1.2 \times 10^5$ cells pr·mL. The concentration of viable cells (the cells stained by DACM, FIG. 6B) was determined to be $2.7 \times 10^6$ cells pr·mL. Based on this, the viability of the cells in the sample was found to be 95.6%. The concentration of cells expressing GFP was determined to be 2.6×10⁶ cells pr·mL and the transfection efficiency was thus found to be 96%.

A mixture of transfected and untransfected MCF-7 cells were also investigated using a fluorescent microscope (FIG. 7). The figure consist of an overlay of images of the same cells captured using different filter cubes for detection of DACM (UV band pass), GFP (blue band pass) and PI (green long pass). As can be seen from the figure, DACM stains viable cells including the cells expressing GFP, while dead cells are only stained by PI.

Conclusion.

Thiol-reacting probes such as DACM can be used in an assay for determining transfection efficiency and combined with an impermeable stain such as PI, information about viability of the cells investigated can also be obtained.

Example 14

Figure 15:
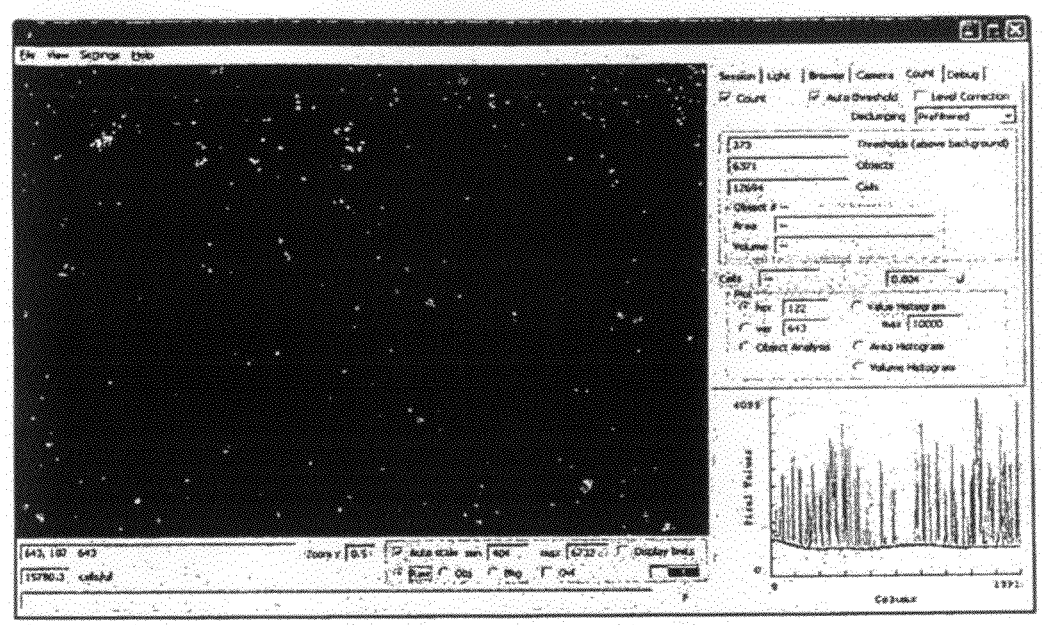
FIG. 15 illustrates quantification of cellular DNA using the claimed apparatus and FACSCalibur™ flow cytometer (BD Biosciences). MCF-7 cells were fixed with ethanol, treated with Rnase A and stained with propidium iodide prior to analysis by the claimed apparatus (A+B) and flow cytometry (C). A) Image captured by the claimed apparatus (2× magnification) B) DNA content histogram obtained from the claimed apparatus displaying fluorescence intensity as a function of cell number. C) DNA content histogram obtained from FACSCalibur.
Figure 15:
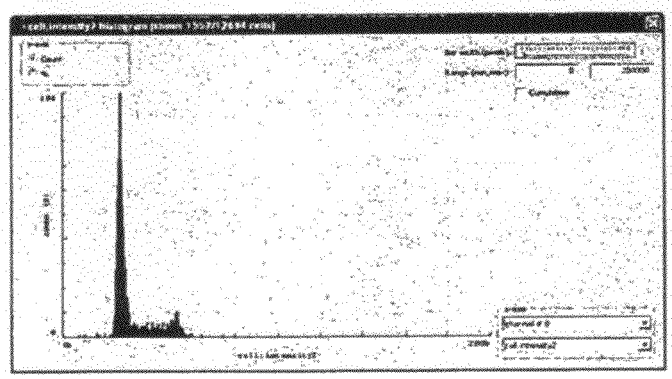
Figure 15:
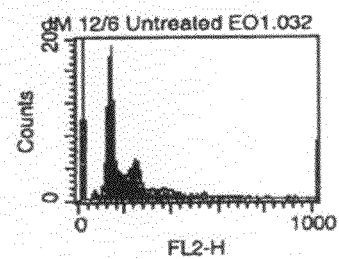
Figure 16:
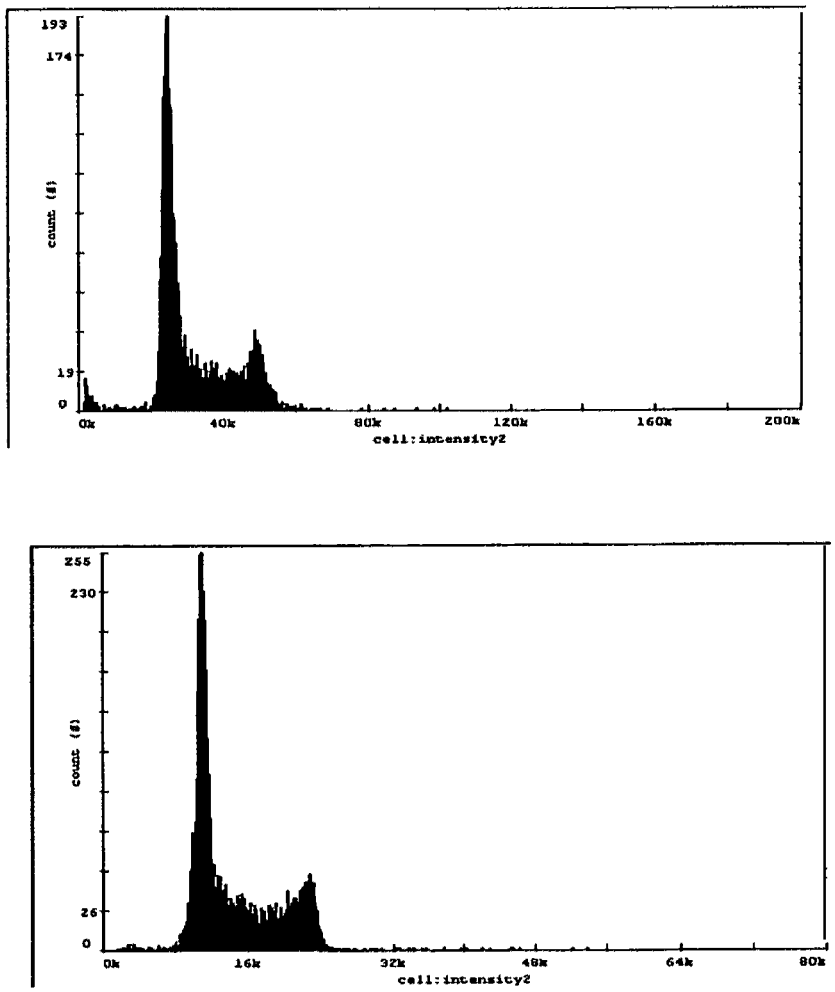
FIG. 16 illustrates a comparison of DAPI and PI for quantification of cellular DNA using the claimed apparatus. DNA content histogram obtained from the claimed apparatus displaying fluorescence intensity as a function of cell number. Upper panel: JM cells were fixed with ethanol, treated with Rnase A and stained with propidium iodide prior to analysis by the claimed apparatus. Lower panel: JM cells were fixed with ethanol and stained with DAPI prior to analysis by claimed apparatus.

Quantification of DNA Content Using DAPI or Propidium Iodide (PI) in Mammalian Cells (Refer FIG. 15 and FIG. 16)

The intensity of fluorescence integrated over a DAPI stained cell is in stoichiometric relationship to DNA content. DAPI preferentially binds to double stranded DNA and the quantum yield of DAPI/RNA complexes is only 20% of that of the DAPI/DNA complex. Hence, using DAPI, there is no requirement for removing RNA by Rnase treatment prior to DNA content measurements. This is a prerequisite for other dyes commonly used for measurements of cellular DNA content, such as propidium iodide. DAPI interacts with double stranded DNA by associating with AT clusters in the minor groove. When bound to double-stranded DNA its absorption maximum is at 358 nm and its emission maximum is at 461 nm. Binding of DAPI to DNA produces a 20-fold fluorescence enhancement.

In the example, the DNA content of an adherent cell lines, MCF-7, a suspension cell line, JM (a jurkat derived cell line), was measured using either DAPI or propidium iodide as DNA stain.

Materials and Methods.

MCF-7 cells were grown in RPMI+10% FCS to 80-90% confluency and cells were washed once in PBS, trypsinized and harvested by centrifugation prior to ethanol fixation. JM cells were grown in RPMI+10% FCS to a density of 5.0×10⁵ cells/ml. Cells were harvested by centrifugation and washed once in PBS prior to ethanol fixation. MCF-7 and JM cells were thoroughly resuspended in 0.5 ml PBS and the cell suspensions were each added to 4.5 ml of ice-cold 70% ethanol fixative. Cells were kept in fixative for at least two hours before staining with either DAPI or PI.

For PI Staining.

Cells were harvested by centrifugation for 5 min at 200×g and washed once with PBS. After another centrifugation cells were resuspended in propidiun iodide staining solution (To 100 ml of 0.1% (v/v) Triton X-100 in PBS add 20 mg DNase-free RNase A and 2 mg of propidium iodide) and incubated for 30 minutes at 37° C. prior to analysis by flow cytometry and the claimed apparatus.

For DAPI Staining.

Cells were harvested by centrifugation for 5 min at 200×g and washed once with PBS. After another centrifugation cells were resuspended in DAPI staining solution (To 100 ml of 0.1% (v/v) Triton X-100 in PBS add 0.1 mg 4',6-diamidino-2-phenylindole; DAPI) and directly analysed by the claimed apparatus.

Results.

Rnase A treated and PI stained MCF-7 cells were analysed by the claimed apparatus and standard flow cytometry. As shown in FIG. 15, the claimed apparatus provides accurate and precise data on cellular DNA content that is comparable with that obtained by flow cytometry, the method of which is the most commonly used for quantification of DNA. Next, MCF-7 cells from the same culture were stained directly with DAPI (no Rnase A treatment) and were analysed by using the claimed apparatus. As shown in FIG. 16, the DNA content histogram obtained from, respectively, PI and DAPI stained cells are almost identical. Hence, the claimed apparatus enables quantification of cellular DNA using both PI and DAPI staining.

Example 15

Figure 17:
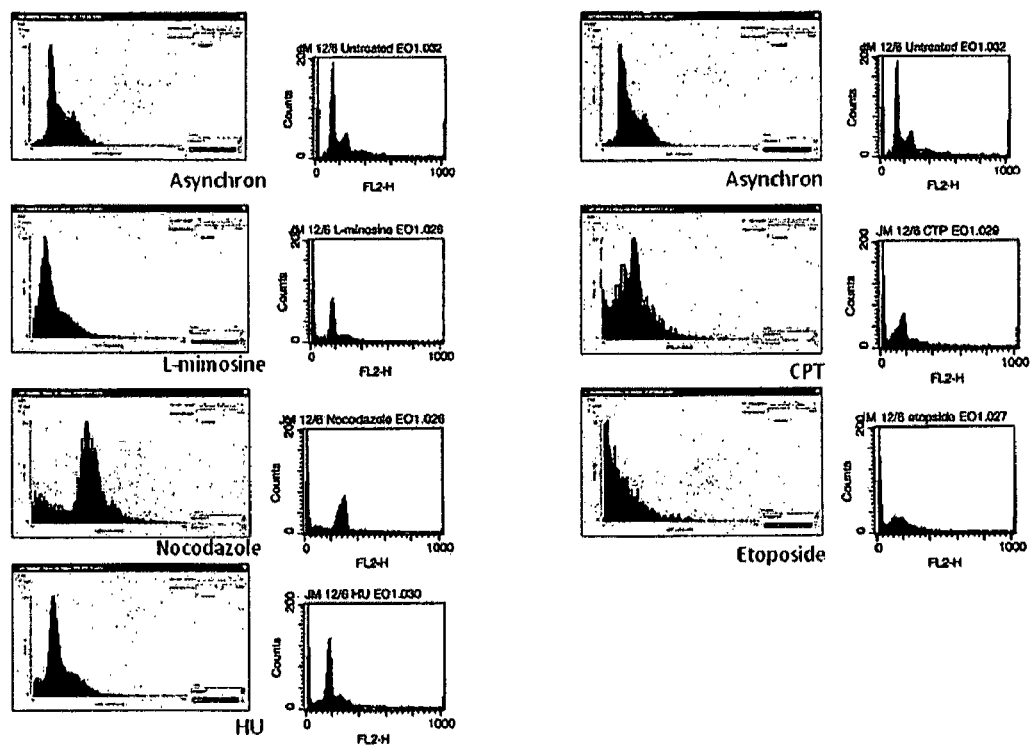
FIG. 17 illustrates DNA histograms of JM cells treated with different drugs. Cellular DNA content was measured using, respectively, claimed apparatus (Grey histograms) and FACSCalibur™ (white histograms)

Effects of Drugs on DNA Content in Mammalian Cells (Refer FIG. 17)

The DNA content of JM cells treated with different drugs was measured using propidium iodide as DNA stain.

Materials and Methods.

JM cells were grown in RPMI+10% FCS to a density of 4.7×10⁵ cells/ml and then either serum starved or treated with the following drugs for 20 hours:

| | |
|---|---|
| 1. Nocodazole (G₂-M arrest): | 0.5 µM |
| 2. L-mimosine (G1): | 0.5 mM |
| 3. Hydroxyurea, HU (S): | 2 mM |
| 4. Camptothecin, CPT (S): | 5 µM |
| 5. Etoposide (S): | 20 µM |
| 6. Untreated control | |

Cells were harvested by centrifugation and washed once in PBS prior to ethanol fixation. Cells were thoroughly resuspended in 0.5 ml PBS and the cell suspensions were each added to 4.5 ml of ice-cold 70% ethanol fixative. Cells were kept in fixative for at least two hours before staining with PI.

For PI Staining.

Cells were harvested by centrifugation for 5 min at 200×g and washed once with PBS. After another centrifugation cells were resuspended in propidiun iodide staining solution (To 100 ml of 0.1% (v/v) Triton X-100 in PBS add 20 mg DNase-free RNase A and 2 mg of propidium iodide) and incubated for 30 minutes at 37° C. prior to analysis by flow cytometry and the claimed apparatus.

Results.

JM cells treated with drugs affecting different phases of the cell cycle were analysed by the claimed apparatus and standard flow cytometry. As shown in FIG. 17, the claimed apparatus provides accurate and precise data on cellular DNA content that is comparable with that obtained from flow cytometry. Hence, the claimed apparatus enables quantification of cellular DNA and may be used for evaluating the effects of different drugs on the cell cycle.

Example 16

Figure 18:
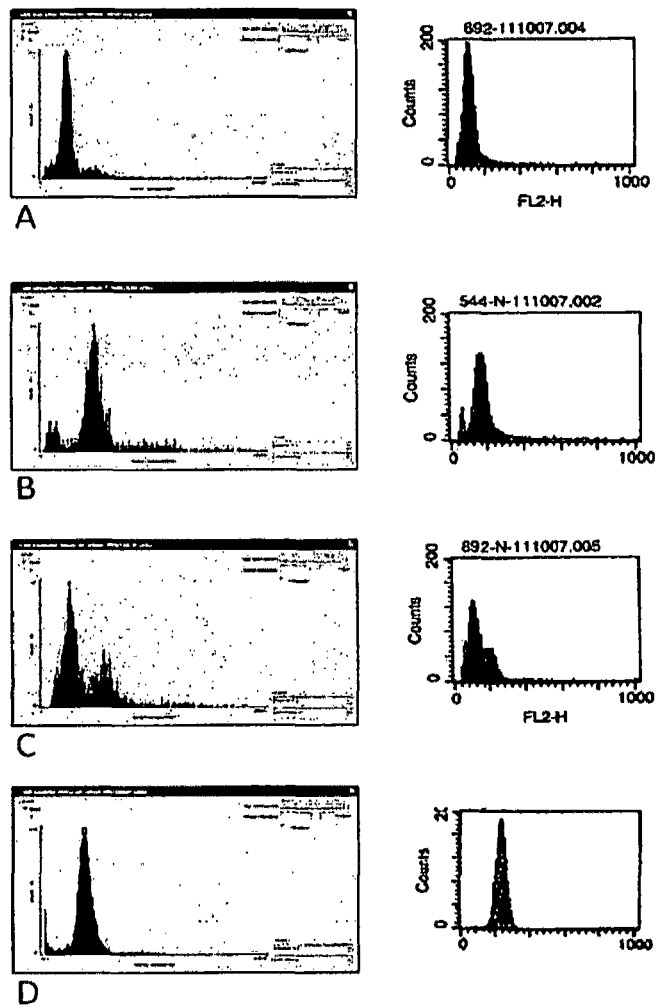
FIG. 18 illustrates DNA histograms of yeast cells (*Schizosaccharomyces pombe*). Cellular DNA content was measured using, respectively, claimed apparatus (Grey histograms) and FACSCalibur™ (white histograms). A) Eg892 incubated at 36° C. for 4 hours in absence of nitrogen. B) Eg544 incubated at 30° C. for 3 hours in absence of nitrogen. C) Eg892 incubated at 36° C. for 4 hours in presence of nitrogen. D) Eg816 incubated at 36° C. for 4 hours in presence of nitrogen (different scale compared to A-C)

Quantification of DNA Content Using Propidium Iodide in Yeast Cells (Refer FIG. 18)

The DNA content of yeast cells (*Schizosaccharomyces pombe*) was measured using propidium iodide as DNA stain. The following two strains were used:
1. Eg544 (CM-SP4), h⁻ Δmat2,3
2. Eg816 (CM-SP7), h⁻ cdc25-22 leu1-32
3. Eg892 (CM-SP27), h⁺ cdc10-V50 ura4-D18

Cdc cells (Eg816 and Eg892) were grown to a density of $5\times10^6$ cells/ml in EMM medium at 25° C. and then incubated at 36° C. (restrictive temperature of cdc mutants) for 4 hours before harvesting and fixation in 70% ethanol. Cdc10 cells were incubated at restrictive temperature both in the presence and absence of nitrogen (EMM-N).

Wild type cells (Eg544) were grown to a density of $5\times10^6$ cells/ml in EMM medium at 30° C., then shifted to EMM and EMM-N (nitrogen starvation) and incubated at 30° C. for 3 hours before harvesting and fixation in 70% ethanol.

Expected arrest point of various cdc mutants at restrictive temperature and of cells starved of nitrogen:
1. Cdc10-V50=$G_1$ arrest: cdc10-V50 cells grown at the restrictive temperature will arrest in $G_1$ with a 1C DNA content. The cdc10-V50 allele is leaky and a minority of the cells in the population will still be dividing. To get a complete $G_1$ arrest the cdc10-V50 cells have to starved of nitrogen.
2. Cdc25-22=$G_2$ arrest=Cdc25-22 cells grown at the restrictive temperature will arrest in $G_2$ with a 2C DNA content.
3. Nitrogen starved cells=$G_1$ arrest
4. Vegetatively growing wild type cells (Eg544) spend most of their time in the $G_2$ phase of the cell cycle and, hence, the majority of the cells in the population will have a 2C DNA content. Upon nitrogen starvation wild type cells will arrest in $G_1$ with a 1C DNA content. A complete $G_1$ requires numerous hours of starvation. In this experiment the cells are only starved for 3 hours and therefore only few cells will be arrested in $G_1$ with a 1C DNA content.

DNA Content Analysis.

About $3\times10^6$ ethanol-fixed cells were Rnase-treated (0.1 mg/ml RNase A in 50 mM sodium citrate, pH 7.0 over night at 37° C.), stained with propidium iodide (4 µg/ml PI in 50 mM sodium citrate, pH 7.0), sonicated for 10 seconds and analysed by flow cytometry (10.000 cells were counted using a Becton-Dickinson FACSCalibur) and the claimed apparatus.

Results.

Yeast cells arrested at different stages of the cell cycle were analysed by the claimed apparatus and standard flow cytometry. As shown in FIG. 18 the claimed apparatus provides accurate and precise data on cellular DNA content that is comparable with that obtained by the flow cytometry. Hence, the claimed apparatus enables quantification of DNA content in yeast cells and can be used for studying e.g. regulation of the cell cycle.

Example 17

Figure 19:
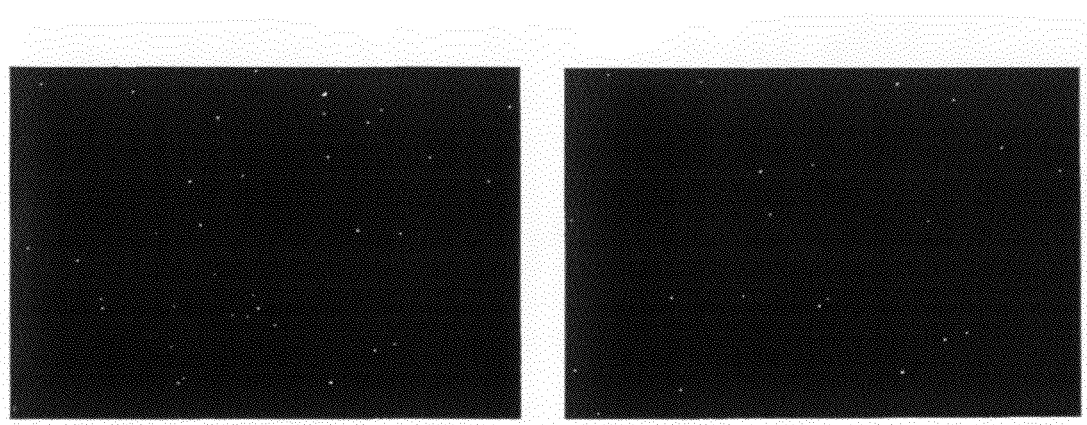
FIG. 19 illustrates at Left; Apoptotic cells stained with AlexaFluor 488-labelled Annexin V. Right; Non-viable cells stained with PI. Pictures captured using the claimed apparatus at 2× magnification.
Figure 20:
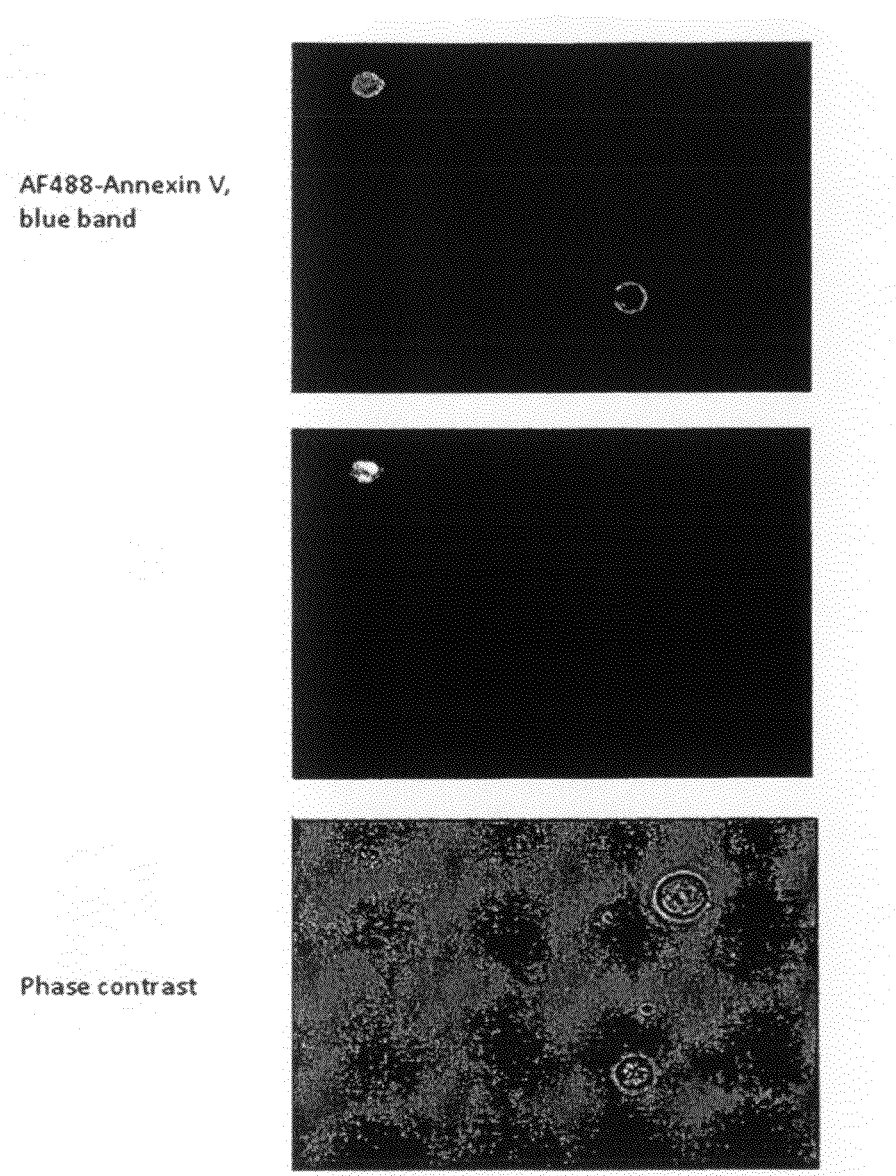
FIG. 20 illustrates fluorescent microscopy and phase contrast of Jurkat cells treated with Camptothecin and stained AF-488 labelled Annexin and PI. Cells are micrographed at 40× magnification.

Apoptosis Assays Annexin V (Refer FIG. 19 and FIG. 20)

An assay for detection of early apoptosis is based on the fact that phosphatidylserine (PS) in healthy, non-apoptotic cells predominantly are located on the internal leaflet of the plasma membrane facing the cytosol. Early in the apoptotic process while the cell membrane are still intact, the PS are translocated to the outer layer of the membrane. Annexins are group of cellular proteins that bind to phospholipids in a calcium-dependent manner, and a member of this group; Annexin V has proven to be a useful tool in detecting apoptotic cells since it preferentially binds to negatively charged phospholipids like PS and shows minimal binding to phosphatidylcholine and sphingomyeline.

By conjugating a fluorescent label to Annexin V it is possible to identify and quantitate apoptotic cells. Annexin V will also bind to PS on late apoptotic and necrotic cells but as the membrane integrity on these cells has been lost, these can be distinguished from early apoptotic cells by the use of an impermeant dye such as PI or DAPI.

Here the claimed apparatus is used in assay fluorescently labeled Annexin V to stain apoptotic and necrotic cells and PI to distinguish between the early and late apoptotic/necrotic cells.

Materials and Methods.

Jurkat (JM) cells were cultivated at 37° C. in a humidified air atmosphere with 5% $CO_2$ in RPMI (Invitrogen, Cat. No. 61870) supplemented with 10% heat-inactivated fetal bovine serum (Invitrogen, Cat. No. 10108-165). 3 µM Camptothecin (Sigma, Cat. No. C-9911) was added to the cells in order to induce apoptosis. After three hours incubation (37° C., 5% $CO_2$) cells were harvested in cold phosphate-buffered saline (PBS) and stained with AlexaFluor 488-labelled Annexin V from the Vybrant® Apoptosis Assay Kit #2 (Molecular probes, V13241) according to the manufacturer's protocol. The stained cells were loaded into a cassette containing propidium iodide. The cassette was placed in the claimed apparatus and the cells were counted and investigated using the claimed apparatus and in-house developed software. The cells were also investigated using an Olympus IX50 fluorescent microscope. Images were captured using a Lumenera CCD camera and in-house developed software. AF488 fluorescence was detected using a U-MWIBA3 (blue bandpass) filter cube (Olympus) and PI fluorescence was detected using a U-MWG2 (green longpass) filter cube (Olympus).

Results.

Using the software associated with the claimed apparatus, the concentration of apoptotic cells (Annexin V conjugate binding cells) was determined to be $2.6\times10^5$ while the concentration of non-viable cells was found to be $4.5\times10^4$ (see FIG. 19). Investigating the cells under fluorescence microscope three types of cells was found: Cells only visible at phase contrast (viable cells), cells positive for both PI and fluorescently labeled Annexin V (necrotic or late apoptotic cells) and finally cells excluding PI but positive for staining with fluorescently labeled Annexin V (early apoptotic cells) (see FIG. 20).

Alternative Methods.

An alternative method for determining the ratio of apoptotic cells to the total number of cells is combining the above described method of Example 17 with a stain for all cells such as acridine orange (AO) or a stain only staining viable cells such as DACM. For example, all cells are stained with AO or another compound staining all cells, combined with fluorescently labelled Annexin V to stain apoptotic cells and an impermeant stain, staining non-viable cells or all viable cells are stained with DACM or another thiol reacting probe, combined with fluorescently labelled Annexin V to stain apoptotic cells and an impermeant stain, staining non-viable cells.

Example 18

Detection Early Apoptosis by Monitoring Changes in the Mitochondrial Membrane Potential A very early event in apoptosis is collapse of the electrochemical gradient across the mitochondrial membrane followed by uncoupling of the respiratory chain. In order to distinguish healthy and apoptotic cells a simple assay based on this phenomenon is to stain the cells using cationic dyes such as 5,5',6,6'-tetrachloro-1,1',3,3'-tetraethylbenzimidazolcarbocyanine iodide (JC-1) or tetramethylrhodamine methyl ester perchlorate or other compounds which fluoresces differently in the two populations. One of the examples is JC-1 in healthy, non-apoptotic cells found in the mitochondrial matrix where it forms red fluorescent aggregates. However, in the event of a fall in the mitochondrial membrane potential (e.g. in connection to apoptosis) the dye returns to its monomeric form which is associated with a large emission shift to green.

For the analysis of changes in mitochondrial membrane potential and hence apoptosis, the cells are incubated with the chosen cationic dye (e.g. JC-1) and analyzed at relevant wave lengths using the claimed apparatus. If, for example, using JC-1 the shift from red to green are quantitated in order to determine the apoptotic cell population. A cell impermeable DNA stain (like DAPI) may be included to stain necrotic cells.

Example 19

Figure 23:
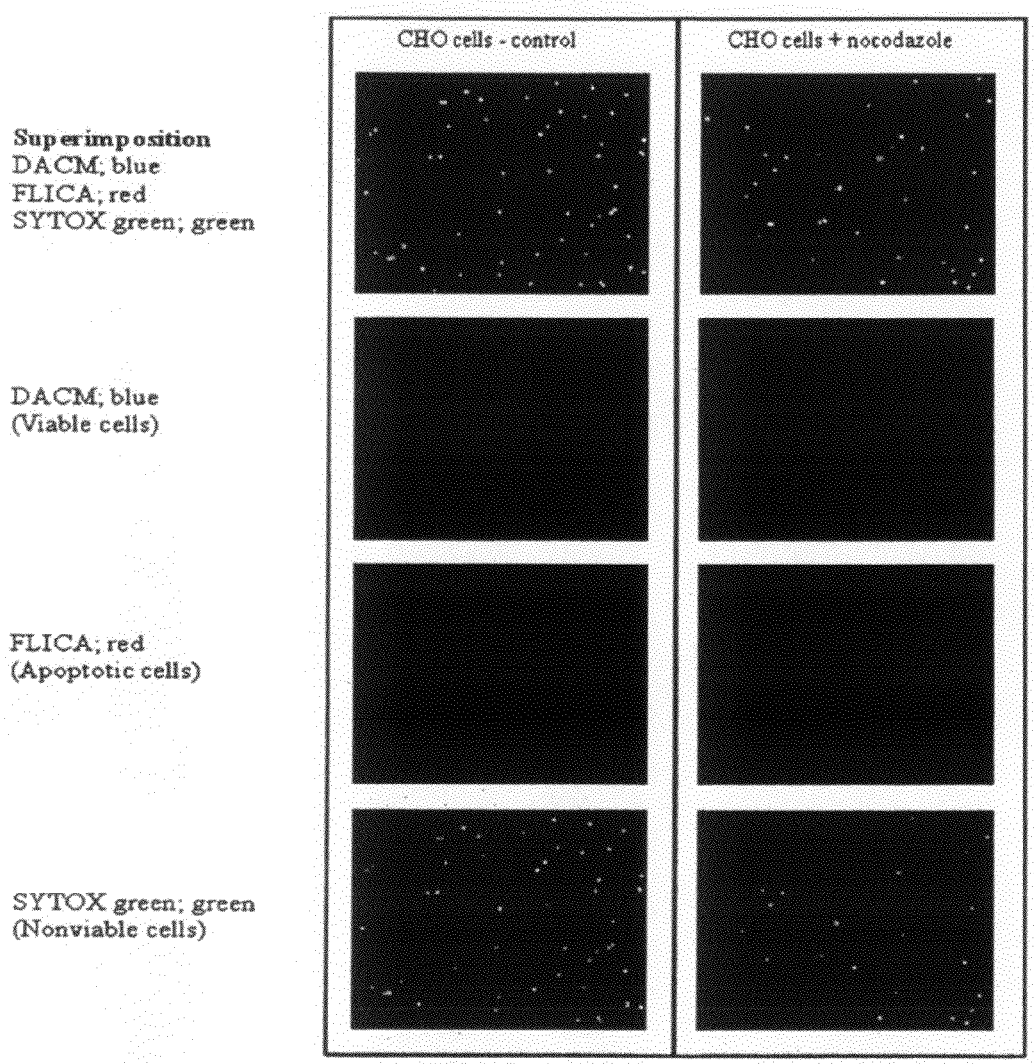
FIG. 23 illustrates images captured using the claimed apparatus, 8× magnification. Cells were stained with DACM (viable cells, blue), SR-VAD-FMK poly-caspase FLICA (apoptotic cells, red) and SYTOX green (nonviable cells green). Left column shows images of untreated CHO cells, right column shows nocodazole treated cells.

Caspase Based Assays (Refer FIG. 23)

Another early marker of apoptosis is the activity of caspases. Caspases are a family of cysteine aspartic acid specific proteases. The caspases mediate cell death and play essential roles in apoptosis, necrosis and inflammation. Caspases are regulated at a post-translational level, and can thus be rapidly activated. The recognition site for caspases is marked by three to four amino acids followed by an aspartic acid residue, with the cleavage occurring after the aspartate. Caspases are activated by proteolytic cleavage of a precursor, and since the cleavage site within precursors matches the specificity of caspases, sequential activation of precursors by activated caspases can occur.

A way to measure the activity of the different types of caspases is to use a peptide substrate containing the recognition site of the caspase of interest linked to a probe which changes fluorescent properties after cleavage at the aspartic acid residue.

A key mediator of apoptosis is caspase-3 (CPP32, apopain, YAMA) which amplifies the signal from initiator caspases such as caspase-8. An example of a fluorogenic substrate for caspase-3 is acetyl Asp-Glu-Val-Asp (acetyl-DEVD) 7-amido-4-methylcoumarin, which upon cleavage results in the release of the fluorescent 7-amino-4-methylcoumarin (AMC) moiety. The caspase activity can thus be quantitated be measuring the fluorescence. The activity of other caspases can also be determined applying the same concept.

Using the claimed apparatus to quantitate caspase activity by this method, the cells are permeabilised/lysed and incubated with the fluorogenic substrate corresponding to the caspase(s) of interest. After incubation fluorescence of the cells are determined using the claimed apparatus and used as a measure for caspase activity.

Another caspase based apoptosis assay is the FLICAssay (Fluorochrome Inhibitor of Caspases Assay). This assay detects active caspases inside the cell using a caspase specific inhibitor sequence linked to a fluorescent probe. The non-cytotoxic caspase specific inhibitor is cell permeant and passes through the intact plasma membrane and covalently binds to the reactive cysteine residue on the large subunit of the active caspase heterodimer. Unbound caspase specific inhibitor diffuses out of the cell and is washed away, thus there is no interference from pro-caspases or inactive forms of the enzyme. Measuring the fluorescence thus gives a direct measure of the amount of active caspase in the whole living cell.

To quantify caspase activity by the FLICAssay, the cells to be investigated are incubated with the chosen caspase specific inhibitor sequence linked to a fluorescent probe. Cells are washed to remove unbound inhibitor and the fluorescence of the cells is determined using the claimed apparatus thereby making measurement of caspase activity on the single cell level possible. Stains for viable/all cells such as DACM or AO and/or nonviable cells such as DAPI/PI may be included in the assay.

Materials and Methods.

CHO cells were cultivated in RPMI (Invitrogen, Cat. No. 61870) supplemented with 10% heat-inactivated fetal bovine serum (Invitrogen, Cat. No. 10108-165) at 37° C. in a humidified air atmosphere with 5% $CO_2$. At 80% confluency cells were either treated with 1 μM nocodazole (Sigma, Cat. No. M1404) or left untreated. After 16 hours incubation cells were harvested in cold phosphate-buffered saline (PBS) and stained with SR-VAD-FMK poly-caspase FLICA (Immunochemistry Technologies, #91) according to the manufacturer's protocol. After staining all viable cells were co-stained using DACM (N-(7-dimethylamino-4-methyl-3-coumarinyl)-maleimide, WAKO Pure Chemical Industries, CAS no. 55145-14-7) and nonviable cells were stained with SYTOX green (Invitrogen, S7020). The stained cells were loaded into a NC-Slide. The NC-Slide was placed in the claimed apparatus and the cells were counted and investigated using the claimed apparatus and in-house developed software. The cells were also investigated using an Olympus IX50 fluorescent microscope. Red fluorescent (apoptosis positive) cells were detected using a U-MWG2 (green longpass) filter cube (Olympus), DACM positive cells were detected using the U-MNUA2 (UV band pass) filter cube (Olympus) and SYTOX green fluorescent cells were detected using a U-MWIBA3 (blue bandpass) filter cube (Olympus).

Results.

Using the software associated with the claimed apparatus, the concentration of apoptotic cells—based on caspase activity—was determined for both the nocodazole treated and the untreated cells. Substantially more nocodazole treated cells exhibited strong red fluorescence than untreated cells (see FIG. 23). This observation was supported by visual inspection using the fluorescence microscope Example 20

Tunel

A characteristic of late stage apoptosis is the fragmentation of nuclear chromatin which results in a multitude of 3'-hydroxyl termini of DNA ends. Thus, a method commonly used for detection of late apoptosis is TUNEL (Terminal deoxynucleotidyl Transferase Biotin-dUTP Nick End Labeling). The TUNEL method involves terminal deoxynucleotidyl transferase to transfer biotin-dUTP or fluorescently marked dUTP to the strand breaks of cleaved DNA. When using biotin-dUTP the biotin-labeled cleavage sites are further reacted with fluorescently conjugated avidin or streptavidin (e.g. FITC avidin) to enable detection and quantification of DNA degradation and thus apoptosis. Using fluorescently marked dUTP this is done directly. Non-apoptotic cells incorporate low levels of labelled-dUTP due to absence of exposed 3'-hydroxyl DNA ends in these cells.

As the terminal deoxynucleotidyl transferase has to enter the cell, the plasma membrane has to be permeabilized prior to the enzymatic reaction. To avoid that this leads to loss of the fragmented DNA, the cells are fixed with either formaldehyde or glutaraldehyde before permeabilization. This fixation crosslinks the DNA to other cellular components and precludes its extraction during permeabilization. Thus the procedure for detecting late apoptosis using the claimed apparatus is as follows: The cells to be investigated are fixated and then permeabilized. The cells are then incubated with terminal deoxynucleotidyl transferase and dUTP labeled with the preferred marker (biotin, fluorescent probe or antibody). During the incubation the terminal deoxynucleotidyl transferase catalyzes the binding of dUTP to the 3'-hydroxyl ends in the DNA. After washing the stained cells are investigated using the claimed apparatus thereby making measurement of apoptosis on the single cell level possible. Stains for all cells such as DAPI, PI or AO may be included in the assay (As the cells are permeabilized permeant as well as impermeant stains may be use).

Example 21

Cell Proliferation

Cell proliferation is the measurement of the number of cells that are dividing in a culture. Rapid and accurate assessment of cell proliferation is a requisite in many experimental set-ups and is very useful for evaluating e.g. the cytotoxic, mutagenic and carcinogenic effects of chemical compounds on eukaryotic cells and for estimating cell doubling time and verify the health of cell cultures. One way of estimating this parameter is by measuring growth curves, however, this is both tedious and time consuming. A second way to analyze cell proliferation is by using DNA synthesis as a marker for proliferation. In these assays, the incorporation of nucleotide-analogues into DNA is quantified. Incorporation of the nucleotide-analogue into DNA is directly proportional to the amount of cell division occurring in the culture.

In one method of analysis cells are incubated with bromodeoxyuridine (BrdU) during the final 2 to 24 hours of incubation. BrdU will be incorporated into the DNA of dividing cells and will be detected and quantified using an anti-BrdU antibody. In order to facilitate antibody binding to the incorporated BrdU, cells are permeabilized and the DNA is denatured by a one-step fixative/denaturing solution. After antibody incubation unbound antibody is washed away and a fluorochrome-conjugated secondary antibody (e.g. FITC labelled antibody) which recognizes the anti-BrdU antibody is added to the solution. Unbound secondary antibody is washed away and the cellular fluorescence is detected and quantified using the claimed apparatus. The intensity of the fluorescent signal is proportional to the amount of incorporated BrdU in the cells. In addition to evaluation of cell proliferation, information about e.g. cell number and cellular antigens can be obtained from the same sample at the single cell level.

A third way to analyse cell proliferation involves labelling of cells with a fluorescent dye that is retained within the cell without affecting cellular function. For each round of cell division, the intensity of the fluorescence is decreased by half.

In one method of analysis cells are incubated with amine reactive diacetate succinimidyl esters (commonly referred to as SE), that diffuses freely into cells. The fluorescent dyes react with intracellular proteins as well as proteins present on the cell surface. Upon reaction the fluorescent dyes are covalently linked to the proteins and are, thus, retained within the cell. The cellular fluorescence is detected and quantified using the claimed apparatus and as a cell divides the fluorescence intensity is decreased by half. In addition to evaluation of cell proliferation, information about e.g. cell number, viability and cellular antigens can be obtained from the same sample at the single cell level. E.g. a cell impermeable DNA stain (like DAPI) can be included in the assay to discern the percentage of cells that are dead.

Example 22

Detection and Quantification of Flourescent Proteins, Hereunder FRET Analysis

A wide range of fluorescent protein variants have now been developed that feature fluorescence emission spectral profiles spanning almost the entire visible light spectrum. Mutagenesis of the original green fluorescent protein (GFP) isolated from the jelly fish *Aequorea victoria* have resulted in new fluorescent probes that range in color from blue to yellow and are some of the most widely used in vivo reporter molecules in biological research. Longer wavelength fluorescent proteins, emitting in the orange and red spectral regions, have been developed from the marine anemone *Discosoma striata* and reef corals belonging to the class Anthozoa. The claimed apparatus can detect the known fluorescent proteins, including BFP, CFP, GFP, GFP-uv, YFP, HcRed1, KFP1, mRFP1, mCherry and other variant derived from dsRED.

In one method of analysis the coding region of the fluorescent protein is linked to a promoter (or enhancer) from a gene of interest. The fusion construct is transfected into a host cell and the fluorescence emitted by the produced fluorescent protein is readily detected and quantified by the claimed apparatus. The intensity of the fluorescent signal is proportional to the expression level of the fluorescent protein, which again is a measure of the activity of the gene of interest. Hence, this method can be used to study transcriptional activity of a gene of interest under various growth conditions.

In a second method of analysis the coding region of the fluorescent protein is linked to the coding region or part of the coding region from a gene of interest. The construct is transfected into a host cell and the fluorescence emitted by the produced fusion protein is detected and quantified by the claimed apparatus. The intensity of the fluorescent signal is proportional to the expression level of the fluorescent fusion protein, which again is a measure of the level of the protein of interest. This method can be used to study dynamic of a protein of interest, such as measurement of protein stability and protein half-life under various growth conditions.

The use of fluorescent protein enables the study of dynamic molecular protein-protein interactions within living cells. One way of detecting molecular interactions involves fluorescence resonance energy transfer (FRET) between two fluorescent proteins or between a single fluorescent protein and a second fluorophore. For example, YFP and CFP can function as a donor-acceptor pair for FRET, in which excitation of the donor (cyan) molecule leads to emission from the acceptor (yellow) molecule, provided that the proteins are close enough for energy transfer to occur. FRET can therefore be used to monitor direct protein-protein interactions between EYFP and ECFP fusion proteins in cells. In one method of analysis the coding region of Cyan Fluorescent Protein (CFP) is linked to the coding region or part of the coding region from one gene of interest. Likewise, the coding region of Yellow Fluorescent Protein (YFP) is linked to the coding region or part of the coding region from a second gene of interest. The two fusion proteins are co-expressed in a host cell. CFP is excited by violet light and yellow light emitted from YFP is detected and quantified.

Example 23

Detection and Quantification of DNA and RNA Markers Using FISH

Fluorescence microscopy at low magnification is very useful for obtaining precise and accurate information about gene amplification and expression levels of RNA markers in cell populations using fluorescent in situ hybridisation (FISH).

In one method of analysis cells are permeabilized and the DNA is denatured by a one-step fixative/denaturing solution facilitating the hybridisation of specific nucleotide probes, such as DNA, RNA, PNA and LNA, labelled with a fluorochrome (e.g. FITC labelled antibody). After hybridisation unbound fluorochrome-conjugated probe is washed away and the cellular fluorescence is detected and quantified using the claimed apparatus. The intensity of the fluorescent signal is proportional to the amount of the DNA or RNA marker present in the cells. The method can be used for detection and quantification of DNA amplification, e.g. HER2 and TOP, and of RNA levels, e.g TERT mRNA. In addition to evaluation of DNA and RNA markers, information about e.g. cell number, DNA content and antigens can be obtained from the same sample at the single cell level.

Example 24

Figure 21:
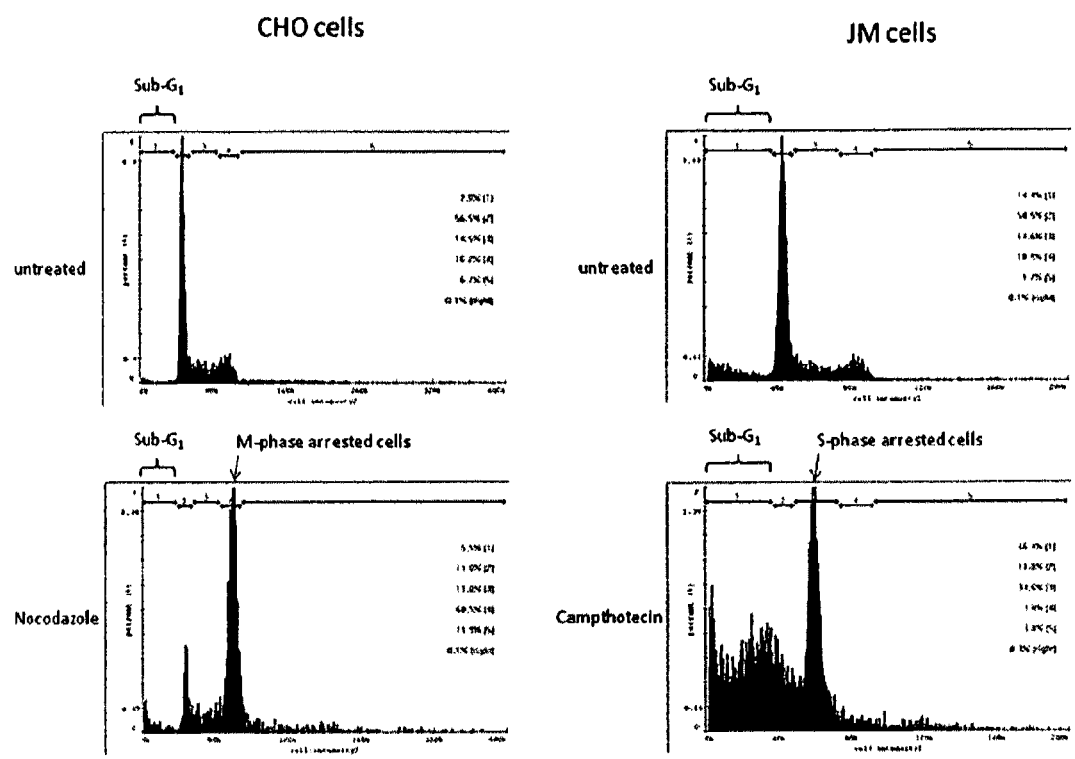
FIG. 21 illustrates DNA histograms of CHO cells (left panel) and JM cells (right panel) treated with different drugs. CHO and JM cells were grown in the absence or presence of, respectively, nocodazole and campthotecin. Cells were stained with DAPI and the DNA content was quantified using the claimed apparatus. Cells arrested in M-phase and S-phase are indicated on the figure. Cells with fragmented DNA (less than 2C DNA content) are marked as sub-$G_1$ cells.

Effects of Drugs on DNA Content in Mammalian Cells (Refer FIG. 21)

The DNA content of CHO cells treated with Nocodazole (inhibitor of M-phase) and JM cells treated with camptothecin (inhibitor of S-phase) was measured using DAPI as DNA stain.

Materials and Methods.

CHO cells were grown in RPMI+10% FCS to 80-90% confluency and treated with 0.5 µM nocodazole for 24 hours. Cells were washed once in PBS, trypsinized and harvested by centrifugation prior to ethanol fixation. JM cells were grown in RPMI+10% FCS to a density of $5.0 \times 10^5$ cells/ml and treated with 5 µM camptothecin for 16 hours. Cells were harvested by centrifugation and washed once in PBS prior to ethanol fixation. CHO and JM cells were thoroughly resuspended in 0.5 ml PBS and the cell suspensions were each added to 4.5 ml of ice-cold 70% ethanol fixative. Cells were kept in fixative for at least two hours before staining with DAPI. For DAPI staining cells were harvested by centrifugation for 5 min at 200×g and washed once with PBS. After another centrifugation cells were resuspended in DAPI staining solution (To 100 ml of 0.1% (v/v) Triton X-100 in PBS add 0.1 mg 4',6-diamidino-2-phenylindole; DAPI) and directly analysed by the claimed apparatus.

Results.

DNA content of CHO and JM cells treated with drugs affecting different phases of the cell cycle were analysed by the claimed apparatus. As shown in FIG. 21, the claimed apparatus provides accurate and precise data on cellular DNA content and can be used for evaluating the effects of different drugs on the cell cycle. Moreover, the claimed apparatus can be used for identifying cells with fragmented DNA (so-called sub-$G_1$ cells). DNA fragmentation is one hallmark of apoptotic cell death.

Example 25

Figure 22:
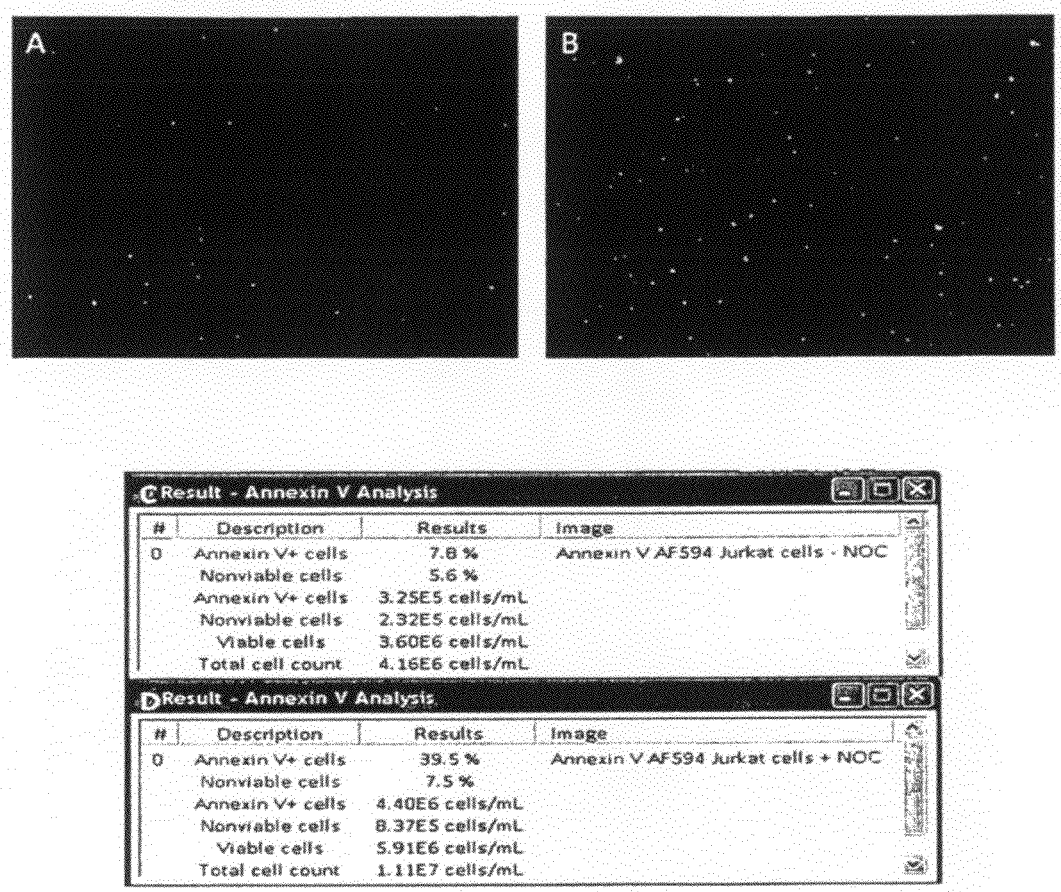
FIG. 22 illustrates images captured using the claimed apparatus, 2× digital and 2× optical magnification. Cells stained with an AF594-annexin V conjugate (apoptotic cells, red) and co-stained with DACM (viable cells, blue) and SYTOX green (non-viable cells, green). A) Untreated jurkat cells; less than 10% AF594-annexin V conjugate positive cells. B) Nocodazole treated jurkat cells; almost 40% AF594-annexin V conjugate positive cells. C) and D) Result box showing the percentage of annexin V positive cells, nonviable cell count and total cell count of untreated and nocodazole treated cells, respectively.

Apoptosis Assays Annexin V (Refer FIG. 22)

Here the claimed apparatus is used in assaying fluorescently labelled annexin V to stain apoptotic and necrotic cells and SYTOX green to distinguish between the early and late apoptotic/necrotic cells. In addition DACM is used to stain all viable cells.

Materials and Methods.

Jurkat cells were cultivated at 37° C. in a humidified air atmosphere with 5% $CO_2$ in RPMI (Invitrogen, Cat. No. 61870) supplemented with 10% heat-inactivated fetal bovine serum (Invitrogen, Cat. No. 10108-165). Cells were either treated with 1 µM nocodazole (Sigma, Cat. No. M1404) or left untreated. After 16 hours incubation (37° C., 5% $CO_2$) cells were harvested in cold phosphate-buffered saline (PBS) and stained with AlexaFluor 594-labelled annexin V (Molecular probes, A-13203) according to the manufacturer's protocol. After annexin V staining all viable cells were co-stained using DACM (N-(7-dimethylamino-4-methyl-3-coumarinyl)-maleimide, WAKO Pure Chemical Industries, CAS no. 55145-14-7) and nonviable cells were stained with SYTOX green (Invitrogen, S7020). The stained cells were loaded into a NC-Slide. The NC-Slide was placed in the claimed apparatus and the cells were counted and investigated using the claimed apparatus and in-house developed software. The cells were also investigated using an Olympus IX50 fluorescent microscope. SYTOX green fluorescence was detected using a U-MWIBA3 (blue bandpass) filter cube (Olympus), the annexin V AF594 conjugate was detected using a U-MWG2 (green longpass) filter cube (Olympus) and DACM was detected using the U-MNUA2 (UV band pass) filter cube (Olympus).

Results.

Using the software associated with the claimed apparatus, the concentration of apoptotic cells (annexin V conjugate binding cells) was determined for both the nocodazole treated and the untreated cells. Nonviable cells were gated out based on SYTOX green staining. The analysis of the viable cells showed that while less than 10% of the control cells were annexin V positive more than 40% of the nocodazole treated cells were annexin V positive (See FIG. 22), while viability was almost not affected. This observation was supported by visual inspection using the fluorescence microscope.

Example 26

Figure 24:
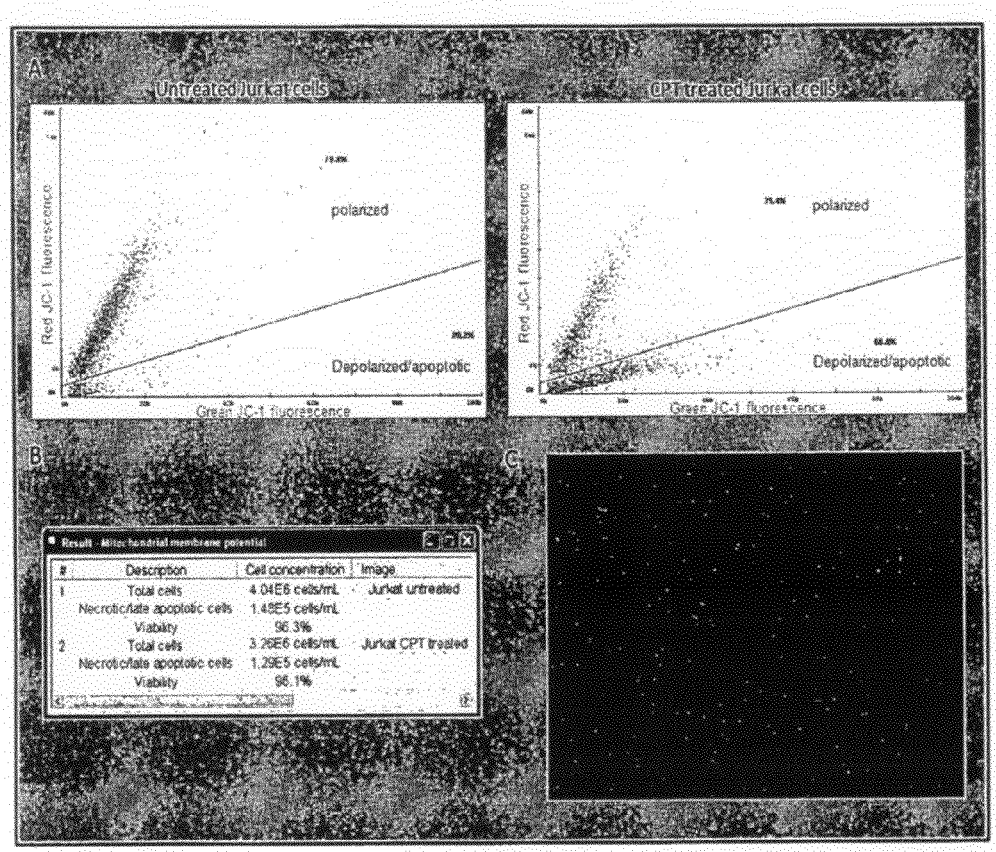
FIG. 24 illustrates Jurkat cells stained with JC-1 and DAPI. Cells were grown in the absence (upper left) or in the presence of 10 μM campthotecin (CPT) for 5 hours at 37° C. (upper right). Cells were stained with 2.5 μg/ml JC-1 for 10 minutes at 37° C., washed with PBS, resuspended in PBS+1 μg/ml DAPI and analysed using the claimed apparatus. In this example untreated Jurkat cells are 20% depolarized/apoptotic whereas CPT-treated Jurkat cells are 60% depolarized/apoptotic (A). Counting the number of DAPI positive cells revealed that the viability of the two samples is similar, being approximately 96% (B). (C) shows the image acquired from the CPT-treated sample.

Detection Early Apoptosis by Monitoring Changes in the Mitochondrial Membrane Potential (Refer FIG. 24)

Loss of the mitochondrial membrane potential is known to precede apoptosis and chemical-hypoxia-induced necrosis. The lipophilic cationic dye JC-1 (5,5,6,6-tetrachloro-1,1,3,3-tetraethylbenzimidazol-carbocyanine iodide) display potential-dependent accumulation in the mitochondria and provides a simple, fluorescent-based method for distinguishing between healthy and apoptotic cells. In healthy cells, the negative charge established by the intact mitochondrial membrane potential facilitates the accumulation of JC-1 in the mitochondrial matrix. At high concentrations JC-1 forms aggregates and become red fluorescent. In apoptotic cells the mitochondrial potential collapses and JC-1 localizes to the cytosol in its monomeric green fluorescent form. A cell impermeable DNA stain (like DAPI) can be included to stain necrotic and late apoptotic cells.

Materials and Methods.

Jurkat cells were grown in RPMI+10% FCS to a density of $5.0 \times 10^5$ cells/ml and treated with 10 µM campthotecin (apoptosis inducing drug) for 5 hours. Cells were stained with 2.5

µg/ml JC-1 for 10 minutes at 37° C., washed with PBS, resuspended in PBS+1 µg/ml DAPI and analysed using the claimed apparatus.

Results.

Jurkat cells stained with JC-1 and DAPI were analysed by the claimed apparatus (FIG. 24). Red and green fluorescence were quantified to identify apoptotic cells (FIG. 24A). To estimate the number of nectrotic/late apoptotic cells DAPI (blue) positive cells were counted (FIG. 24B). As shown in FIG. 24, the claimed apparatus can be used to identify cells with collapsed mitochondrial membrane potential and enables the identification of early apoptotic cells.

Example 27

Figure 25:
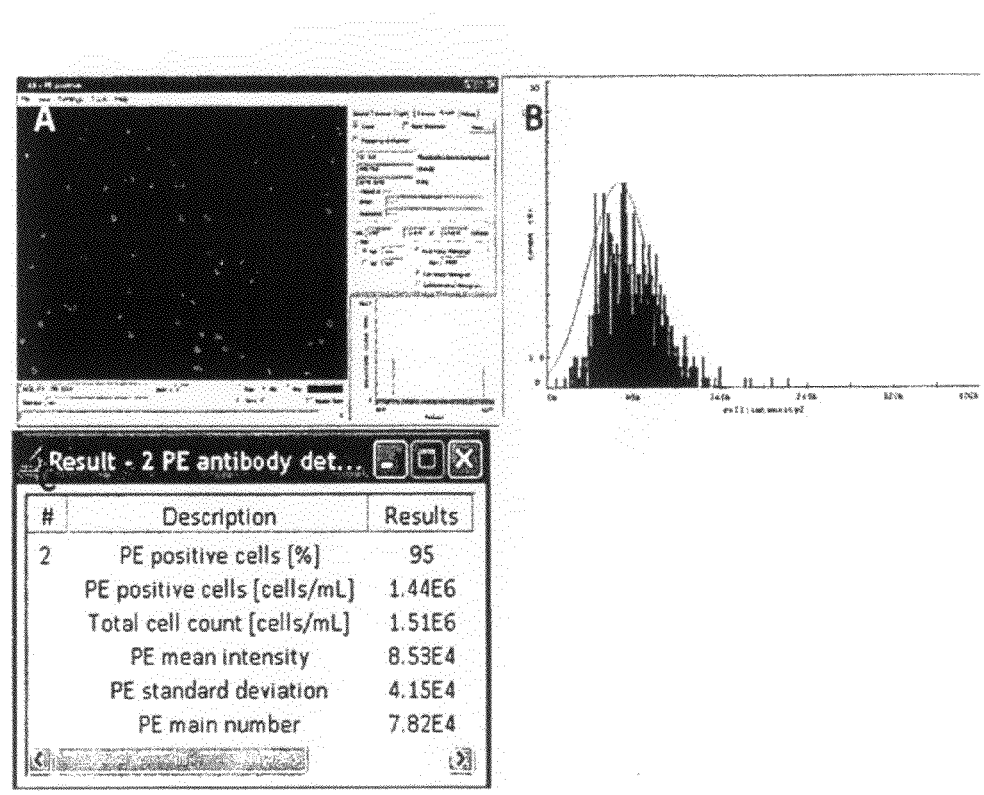
FIG. 25 illustrates A) Contrast image of CD3 positive T cells from human blood was marked using a R-phycoerythrin (PE) secondary conjugate (red/pink). To visualise all viable cells, the cell sample was co-stained using DACM (blue). B) The histogram shows the fluorescence intensity of PE positive cells. C) The result box summarise the information achieved including percentage of positive cells, total cell count, PE mean fluorescence intensity, standard deviation and main number. All data was obtained using the claimed apparatus and associated software.

Detection and Quantification of Antigens (Refer FIG. 25)

Fluorescence microscopy at low magnification is very useful for obtaining precise and accurate information about the expression level of antigens, such as intracellular and cell surface proteins, in cell populations.

An example of this is described in the following. Cells are incubated with a primary antibody recognizing an antigen. After antibody incubation unbound antibody is washed away and a fluorochrome-conjugated secondary antibody (e.g. FITC or PE labelled antibody) which recognizes the primary antibody is added to the solution. Unbound secondary antibody is washed away and the cellular fluorescence is detected and quantified using the claimed aparatus. The intensity of the fluorescent signal is proportional to the amount of the cellular antigen present. The method can be used for detection and quantification of different cellular antigens such as HER2, EGFR, VGFR, UPR and CD molecules including CD3, CD4 and CD8. In addition to antigen evaluation, information about e.g. cell number, viability and DNA content can be obtained from the same sample at the single cell level. Intracellular antigens such as the cancer markers TERT, TOP and Survivin can be detected by a similar method by fixating and permeabilizing the cells prior to incubation with antibody. Instead of combining the detection of intracellular markers with measurement of viability it can be combined with quantification of e.g. DNA content and hence cell cycle profiling.

Materials and Methods.

CD3+ positive T cells were purified from the lymphocyte containing fraction of a Lymphoprep (Axis-Shield, #1114544) separated buffy coat by positive selection with anti-CD3 microbeads (Miltenyi Biotec) according the manufacturers protocol. Cells were then stained with primary CD3 specific antibody and after 30 minutes incubation cells were washed and then stained with R-phycoerithrin (PE) labelled secondary antibody (Antibodies from BD BioSciences). After 30 minutes incubation cells were washed again and all viable cells were co-stained using DACM (N-(7-dimethylamino-4-methyl-3-coumarinyl)-maleimide, WAKO Pure Chemical Industries, CAS no. 55145-14-7). The stained cells were loaded into a NC-Slide. The NC-Slide was placed in the claimed apparatus and the cells were counted and investigated using the claimed apparatus and in-house developed software.

Results.

Using the claimed apparatus to analyse cells purified using CD3-selective microbeads we found that 95% of the cells were stained with the PE conjugated antibody indicating that 95% of all cells expressed CD3 (FIG. 25). This is in accordance with data normally achieved by flow cytometry of cells positively selected by microbead purification.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Throughout the foregoing description, for the purposes of explanation, numerous specific details were set forth in order to provide a thorough understanding of the invention. It will be apparent, however, to one skilled in the art that the invention may be practiced without some of these specific details.

Accordingly, the scope and spirit of the invention should be judged in terms of the claims which follow.

We claim:

1. A method for detecting viability of a test cell, said method comprising:
    mixing the test cell with a combination of 4,6-diamion-2-phenylindole (DAPI) dye or substituted variance of DAPI and Acridine Orange or other stains of Acridine;
    allowing staining of cells for a time period of at the most 60 minutes, such as 30 minutes, such as 20 minutes, such as at most 10 minutes;
    obtaining a stained cell sample, wherein the Acridine Orange/other stains of Acridine stains the entire population of cells and DAPI/substituted variance of DAPI stains only non-viable cell;
    exposing the stained test cell to an excitation light;
    detecting a fluorescence signal from the stained test cell; and
    processing the fluorescence signal to identify whether the test cell is non-viable.

2. The method according to claim 1, wherein the test cell includes a plurality of cells.

3. The method according to claim 2, wherein cell count and non-viability of the plurality of cells are identified by using 4,6-diamion-2-phenylindole (DAPI) dye or substituted variance of DAPI.

4. The method according to claim 1, wherein the test cell is a cultured cell or a primary cell.

5. The method according to claim 1, wherein the test cell is selected from the group consisting of a mammalian cell line, a mammalian cell line in suspension, an insect cell line, a *Drosophila melanogaster* Schneider-2a cell, a human embryonic cell line, a primary cell, and a human blood cell.

6. The method according to claim 1, further comprising coating a sample device with a combination of Acridine Orange dye, or other stains of Acridine, and 4,6-diamion-2-phenylindole (DAPI) dye/substituted variance of DAPI to a combined concentration of 2.5 µg/mL.

7. The method according to claim 1, wherein the Acridine Orange dye stains both viable test cell and non-viable test cell.

8. The method according to claim 1, further comprising preparing the test cell under a controlled environment.

9. The method according to claim 8, wherein the preparation under controlled environment comprises:
    drawing a small sample of human venous blood; and
    diluting the blood sample at least five times in PBS to obtain the test cell.

10. The method according to claim 1, further comprising injecting the test cells into the sample device using a piston.

11. The method according to claim 1, wherein the excitation light is from a source selected from the group consisting of a thermal light source, a halogen lamp, a gas lamp, a xenon lamp, a light emitting diode, a laser, and a laser diode.

12. The method according to claim 1 wherein the processing comprises analyzing the fluorescence signal for number of counts of non-viable cells in the cells.

13. An apparatus to label a test cell, said apparatus comprising:
a sample device coated at least partly with a combination of 4,6-diamion-2-phenylindole (DAPI) dye or substituted variance of DAPI and Acridine Orange dye or other stains of Acridine, wherein the Acridine Orange/other stains of Acridine stains the entire population of cells Acridine stains and the DAPI/substituted variance of DAPI only stains a non-viable cell;
a test cell injecting unit to load the test cell into the sample device;
an excitation unit to expose the injected test cell to an excitation light;
a detection unit to detect a fluorescence signal emitted from the loaded test cell; and
a processor to process the fluorescence signal to assess whether the test is non-viable.

14. The apparatus according to claim 13, wherein the detection unit comprises of at least one detector having a plurality of detection elements.

15. The apparatus according to claim 13, wherein the processor comprises an analyzer to analyze the fluorescence signal for number of counts of non-viable cells.

16. A method for providing information about a cell, said method comprising:
transfecting the cell with a fluorescent protein or fluorescently labelled nucleic acid;
adding and mixing a thiol-reacting molecule and a cell-impermeable DNA stain to the transfected cell to obtain a cell solution;
exposing the cell solution to an excitation light;
detecting an emission light from the cell solution; and
processing the emission light to obtain the information about the cell.

17. The method according to claim 16, wherein the information comprises of transfection efficiency, cell viability and cytotoxicity level.

18. The method according to claim 16, wherein the cell-impermeable DNA stain is selected from a group consisting of propidium iodide, and acridine homodimer.

19. The method according to claim 16, wherein the nucleic acid is selected from the group consisting of a fluorescent protein, and a small interference RNA.

20. The method according to claim 16, wherein the thiol reacting molecule is DACM.

21. The method according to claim 16, wherein the excitation light is an ultra violet/violet light and the emission light is a blue light for determining a viable cell, when the thiol reacting molecule is DACM.

22. The method according to claim 16, wherein:
the excitation light is a green light and the emission light is a red light for determining a non-viable cell, when propidium iodide is used as a cell impermeable DNA stain; and
the excitation light is a blue light and the emission light is a green light for determining a non-viable cell, when acridine homodimer is used as a cell impermeable DNA stain.

23. The method according to claim 16, wherein:
a cell expressing BFP emits blue light when it is excited with UV or violet light;
a cell expressing CFP emits cyan light when it is excited with violet or blue light;
a cell expressing GFP emits green light when it is excited with blue light;
a cell expressing YFP emits yellow light when it is excited with blue or green light;
a cell expressing dsRed or variants thereof emits red light when it is excited with green light;
a cell harbouring siRNA emits blue light when it is excited with UV or violet light;
a cell harbouring siRNA emits cyan light when it is excited with violet or blue light;
a cell harbouring siRNA emits green light when it is excited with blue light;
a cell harbouring siRNA emits yellow light when it is excited with blue or green light; and
a cell harbouring siRNA emits red light when it is excited with green light.

24. The method according to claim 16, wherein the cell includes a plurality of cells.

25. The method according to claim 24, wherein the information about a plurality of cells is identified by using a combination of a fluorescent protein or fluorescently labelled nucleic acid and a thiol-reacting molecule.

26. An apparatus to determine information about a cell, said apparatus comprising:
a transfecting unit to transfect the cell with a fluorescent protein or fluorescently labelled nucleic acid;
a mixing unit to add and mix a thiol-reacting molecule and a cell-impermeable DNA stain to the transfected cell to obtain a cell solution;
an excitation unit to expose the cell solution to an excitation light;
a detection unit to detect an emission light from the cell solution; and
a processor to process the emission light to obtain the information about the cell.

27. The apparatus according to claim 26, wherein the information comprises transfection efficiency, cell viability and cytotoxicity level.

28. A method for determining transfection efficiency, the method comprising:
transfecting the cell with a fluorescent protein or fluorescently labelled nucleic acid;
adding DACM to the transfected cell to obtain a cell solution;
exposing the cell solution to an excitation light;
detecting an emission light from the cell solution; and
processing the emission light to obtain trasfection efficiency about the cell,
wherein the cells are not incubated.

* * * * *